US012678425B2

(12) United States Patent
Ullah et al.

(10) Patent No.: US 12,678,425 B2
(45) **Date of Patent: *Jul. 14, 2026**

(54) METHODS FOR TREATING AGAINST VIRUSES

(71) Applicants: Howard University, Washington, DC (US); GEORGETOWN UNIVERSITY, Washington, DC (US)

(72) Inventors: Hemayet Ullah, Washington, DC (US); Sivanesan Dakshanamurthy, Washington, DC (US)

(73) Assignees: Howard University, Washington, DC (US); GEORGETOWN UNIVERSITY, Washington, DC (US)

( * ) Notice: Subject to any disclaimer, the term of this patent is extended or adjusted under 35 U.S.C. 154(b) by 1038 days.

This patent is subject to a terminal disclaimer.

(21) Appl. No.: 17/606,542

(22) PCT Filed: Apr. 27, 2020

(86) PCT No.: PCT/US2020/030061

§ 371 (c)(1),
(2) Date: Oct. 26, 2021

(87) PCT Pub. No.: WO2020/220018

PCT Pub. Date: Oct. 29, 2020

(65) Prior Publication Data

US 2022/0211673 A1 Jul. 7, 2022

Related U.S. Application Data

(60) Provisional application No. 62/839,402, filed on Apr. 26, 2019.

(51) Int. Cl.

*A61K 31/4196* (2006.01)
*A61K 31/522* (2006.01)
*A61P 31/12* (2006.01)
*A61P 31/22* (2006.01)

(52) U.S. Cl.

CPC ........ *A61K 31/4196* (2013.01); *A61K 31/522* (2013.01); *A61P 31/12* (2018.01); *A61P 31/22* (2018.01)

(58) Field of Classification Search

CPC ........ A61K 31/4196; A61P 31/22; A61P 31/12
See application file for complete search history.

(56) References Cited

U.S. PATENT DOCUMENTS 11,576,901 B2 * 2/2023 Ullah ................. A61K 31/4196
11,596,623 B2 * 3/2023 Ullah ................. A61K 31/4196

FOREIGN PATENT DOCUMENTS

WO 2008/157407 A1 12/2008
WO 2013/151769 A1 10/2013
WO WO-2017165885 A1 * 9/2017 ......... A61K 31/4196

OTHER PUBLICATIONS

Hoggarth, Eric, Journal of the Chemical Society (1952) 4811-17. (Year: 1952).*
Patani et al., "Bioisosterism: A Rational Approach in Drug Design", 1996, Chemical Reviews, 96, pp. 3043-3350 (Year: 1996).*
Tyring et al., "A Randomized, Placebo-Controlled Comparison of Oral Valacyclovir and Acyclovir in Immunocompetent Patients With Recurrent Genital Herpes Infections", 1998, Arch. Dermatol., 134, pp. 185-191 (Year: 1998).*
Al-Soud et al., "In-Vitro Anti-HIV and Antitumor Activity of New 3,6-Disubstituted [1,2,4]Triazolo[3,4-b][1,3,4]thiadiazoles and Thiadiazine Analogues", 2008, Arch. Pharm. Chem. Life Sci., 341, pp. 365-369 (Year: 2008).*
Tang et al.,"Synthesis, antifungal and antibacterial activity for novel amide derivatives containing a triazole moiety," Chemistry Central Journal, 2013, vol. 7, No. 30, pp. 1-7 (7 pages total).
Moorthy et al.,"Synthesis, antifungal evaluation and in silico study of novel Schiff bases derived from 4-amino-5 (3,5-dimethoxy-phenyl)-4H-1,2,4-triazol-3-thiol," Arabian Journal of Chemistry, 2017, vol. 10, pp. S3239-S3244 (6 pages total).
Extended European Search Report issued Jul. 17, 2023 in Application No. 20796172.3.

* cited by examiner

*Primary Examiner* — Jeffrey H Murray
*Assistant Examiner* — Madeline E Braun
(74) *Attorney, Agent, or Firm* — Sughrue Mion, PLLC

(57) ABSTRACT

A combinatorial method for treating against, or at least inhibiting or suppressing, the proliferation of an internal ribosome entry site utilizing virus (IRES-utilizing virus) in a host in need of treatment involves administering the host a compound, a tautomer, or a pharmaceutically acceptable salt thereof, in an amount effective for inhibiting replication of the IRES-utilizing virus in cells, wherein the compound is represented by the formula:

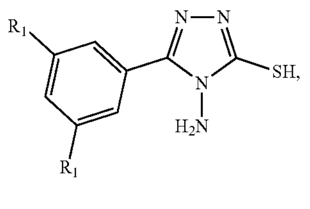

wherein each $R_1$ is independent of the other and represents a halogen atom selected from the group consisting of bromo, chloro, fluoro and iodo; and either separately administering another anti-viral drug and/or pro-drug to the anti-viral drug or co-administering the anti-viral drug and/or the pro-drug with the compound, its tautomer, or its pharmaceutically acceptable salt.

10 Claims, 18 Drawing Sheets

Specification includes a Sequence Listing.

SD-29-12

SD-29-14

24h post infection 48h post infection

Cotransfect, 24h post infection with 10 ul/ml HSV-1 Jan 31 image

METHODS FOR TREATING AGAINST VIRUSES

CROSS REFERENCE TO RELATED APPLICATIONS

This application is a National Stage of International Application No. PCT/US2020/030061, filed Apr. 27, 2020, claiming the benefit of U.S. Provisional Application No. 62,839,402, filed Apr. 26, 2019, the disclosure of which is incorporated by reference herein in its entirety.

FIELD OF THE INVENTION

The present disclosure relates generally to treating an infection with, or inhibiting the proliferation of, an IRES-utilizing virus. In some embodiments, the IRES-utilizing virus is a virus from the family Herpesviridae or Coronaviridae. In some aspects of the present disclosure, the disclosed methods include a combinatorial treatment against an infection with, or for inhibiting the proliferation of, an IRES-utilizing virus, including IRES-utilizing viruses from the family Herpesviridae or Coronaviridae.

BACKGROUND INFORMATION

It has been reported that various viruses use a host's RACK1 (Receptor for activated C kinase 1) protein to translate viral mRNA using a viral mRNA secondary structure known as the Internal Ribosomal Entry Site (IRES). *Cell,* 159(5):1086-1095 (2014); *Virology,* 545:53-62 (2020). Herpes simplex virus (HSV) belongs to the alpha-herpesvirus subfamily, within the family Herpesviridae, and is a common human pathogen that causes recurrent infections through its ability to establish a latent state in sensory ganglia after primary epithelial infection. Chayavichitsilp el al. (*Pediair. Rev.,* 2009, 30:119-129). HSV infects a large population (over 500 million worldwide), and is associated with a variety of diseases and disorders, including, but not limited to: genital herpes (with most cases being caused by HSV-2, and some by HSV-1); ocular herpes (generally induced by HSV-1, and is a leading cause of blindness worldwide); and neonatal herpes (which is usually an infectious consequence of either HSV-1 or HSV-2 via vertical transmission).

One of the characteristics of HSV infection is its ability to latently infect neurons so that it can be reactivated, thereby causing recurrent infections. Although the clinical symptoms of HSV-caused diseases can be controlled with anti-viral drugs or their pro-drugs (e.g., acyclovir and valacyclovir), they are not strong enough to prevent subclinical transmission. Shin (*Trends Immunol.,* 2013, 34:487-494); Johnston et al. (*Lancet,* 2012, 379:641-647). In addition, resistance to acyclovir and valacyclovir frequently occur, and no approved prophylactic or therapeutic vaccine against HSV is available. Therefore, more effective preventive and/or therapeutic drugs against HSV infection are needed.

Additionally, several viruses within the family Coronaviridae are associated with significant morbidity and mortality, for example: MERS-CoV (the beta coronavirus that causes Middle East Respiratory Syndrome, or MERS); SARS-CoV (the beta coronavirus that causes severe acute respiratory syndrome, or SARS); and SARS-CoV-2 (the novel coronavirus that causes coronavirus disease 2019, or COVID-19). Of particular note, SARS-CoV-2 was identified as the cause of an outbreak of viral pneumonia that originated in Wuhan, China in 2019. SARS-CoV-2 subsequently spread across the globe, infecting millions, and resulting in hundreds of thousands of fatalities. Effective treatments for such viruses are also needed.

SUMMARY OF THE INVENTION

The present disclosure addresses the above-described limitations in the art, by providing agents and methods for treating an infection with, or inhibiting the proliferation of, an IRES-utilizing virus, including, for example, an IRES-utilizing virus from the family Herpesviridae or Coronaviridae. Also disclosed herein are combinatorial methods for at least inhibiting or suppressing host RACK1 protein, and methods for treating, and/or inhibiting or suppressing, internal ribosome entry site (IRES)-dependent viral translation.

Some embodiments of the present disclosure include treating, and/or inhibiting or suppressing, viral infection from an IRES-dependent virus from the Herpesviridae or Coronaviridae families of viruses in a host, in a combinatorial method comprising administering an effective amount of a compound, a tautomer, or a pharmaceutically acceptable salt thereof, to the cell(s) for interfering with the interaction of a host's RACK1 protein with at least a portion of the virus genome containing a sequence for a viral Internal Ribosome Entry Site (IRES); and either administering another anti-viral drug and/or pro-drug, or co-administering another anti-viral drug and/or pro-drug, with the compound, its tautomer, or its pharmaceutically acceptable salt.

The compound(s), tautomer(s) or pharmaceutically acceptable salts are believed to target the functional sites of the host's RACK1 protein. It is believed that the treatment increases instability of such protein and can lead to depletion of RACK1 in the ribosome. This aspect of the treatment may stop, or at least inhibit or suppress, viral replication (proliferation or propagation) in infected cells by interfering with the IRES-dependent translation of viral mRNA (e.g., non-capped viral RNA).

In one aspect of the present disclosure, such a method of treating, or at least inhibiting or suppressing, a viral infection from an IRES-utilizing virus, such as from the Herpesviridae or Coronaviridae family of viruses, comprises administering a therapeutically effective amount of a compound, a tautomer thereof, or a pharmaceutically acceptable salt thereof, for interfering with replication of the viral mRNA, in which the compound is represented by the formula (4):

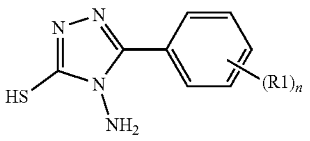

wherein R1 represents a halogen atom, and n is 1 or 2, to a host in need of treatment. When n is 2, each R1 can be the same or different. When n is 2, the phenyl moiety includes 2,4-halogen substituted phenyl, 2,5-halogen substituted phenyl and 3,5-halogen substituted phenyl. The method of treating involves interfering with, or at least inhibiting or suppressing, viral mRNA replication in the infected cells thereby stopping, or at least inhibiting or suppressing, viral proliferation.

In some embodiments, the treatment is a combinatorial treatment, which further comprises either administering an anti-viral drug (e.g., an anti-viral against herpesviruses and/ or coronaviruses), and/or a pro-drug for an anti-viral drug (e.g., against herpesviruses and/or coronaviruses); or co-administering the other anti-viral drug and/or pro-drug for an anti-viral drug with the compound, its tautomer, or its pharmaceutically acceptable salt. It will be appreciated that the anti-viral drug (e.g., an anti-herpes and/or an anti coronavirus drug) preferably has a different mode of action than a compound of a formulae herein. In this and in the other various aspects of a combinatorial method, a therapeutically effective amount of a compound, a tautomer thereof, or a pharmaceutically acceptable salt thereof, for interfering with replication of the viral mRNA, is preferably administered to a host in need of treatment.

In some aspects, in such a combinatorial method of treating, or at least inhibiting or suppressing, a viral infection from an IRES-utilizing virus, such as an IRES-utilizing virus from the family Herpesviridae or Coronaviridae, the compound is represented by the formula (1):

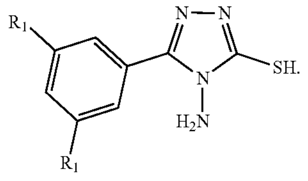

The compound can be in the form of a tautomer(s) or a pharmaceutically acceptable salt. Each $R_1$ represents, independent of the other, a halogen atom at the meta positions on the phenyl ring. This aspect of the combinatorial method of treating involves interfering with, or at least inhibiting or suppressing, viral mRNA replication in the infected cells thereby stopping, or at least inhibiting or suppressing, viral proliferation.

In certain aspects, such a combinatorial method of treating, or at least inhibiting or suppressing, a viral infection from an IRES-utilizing virus, such as an IRES-utilizing virus from the family Herpesviridae or Coronaviridae, includes administering a compound, a tautomer thereof, or a pharmaceutically acceptable salt thereof, for interfering with replication of the viral mRNA, in which the compound is represented by the formula (4A):

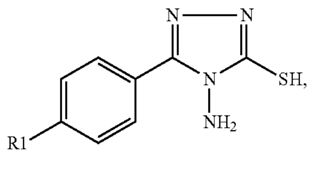

wherein $R_1$ represents a halogen atom at the para position on the phenyl ring. In this aspect of such a combinatorial method of treating, the administration of this compound (or its tautomer(s) and/or pharmaceutically acceptable salt(s)) involves interfering with, or at least inhibiting or suppressing, viral mRNA replication in the infected cells thereby stopping, or at least inhibiting or suppressing, viral proliferation.

In some embodiments of the present disclosure, such a combinatorial method of treating, or at least inhibiting or suppressing, a viral infection from an IRES-utilizing virus, such as an IRES-utilizing virus from the family Herpesviridae or Coronaviridae, includes administering a therapeutically effective amount of a compound or a pharmaceutically acceptable salt thereof for interfering with replication of the viral mRNA, in which the compound is represented by the formula (5):

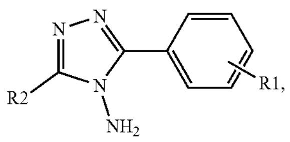

wherein R1 represents —S—$(CH_2)_m$—COOH wherein m is 1, 2, or 3, and R2 represents $C_1$-$C_6$ alkoxy substituted phenyl, in a combinatorial treatment with another anti-viral drug (e.g., an anti-herpes drug) having a different mode of action (or with a pro-drug for the another anti-viral drug) to a host in need of treatment. This aspect of the combinatorial method of treating involves interfering with, or at least inhibiting or suppressing, viral mRNA replication in the infected cells thereby stopping, or at least inhibiting or suppressing, viral proliferation.

A RACK1 inhibitor composition for inhibiting replication of an IRES-utilizing virus (such as an IRES-utilizing virus from the family Herpesviridae or Coronaviridae) in cells comprises a compound, a tautomer, or a pharmaceutically acceptable salt thereof, wherein the compound is represented by any of the formulae herein. The RACK1 inhibitor composition can include an anti-viral drug (e.g., an anti-herpes and/or an anti coronavirus drug) having a different mode of action, or with a pro-drug for the anti-viral drug (e.g., an anti-herpes and/or an anti coronavirus drug).

Non-limiting embodiments of the present disclosure are as follows:

(1) A method for inhibiting the replication of a virus that utilizes an internal ribosome entry site in its replication, comprising administering a compound, a tautomer, or a pharmaceutically acceptable salt thereof, in an amount effective for inhibiting replication of the virus in cells, wherein the compound is represented by the formula:

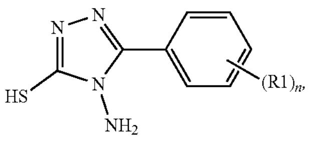

wherein n is 1 or 2, and R1 represents a halogen atom selected from the group consisting of bromo, chloro, fluoro and iodo, and provided that when n is 2 each R1 can be the same or different; and further comprising either separately administering another anti-viral drug and/or pro-drug to the anti-viral drug, or co-administering the anti-viral drug and/or the pro-drug with the compound, its tautomer, or its pharmaceutically acceptable salt.

(2) The method according to (1), wherein n is 2 and the R1 substitution is at the 2,4 positions of the phenyl moiety, the 2,5-positions of the phenyl moiety, or the 3,5-positions of the phenyl moiety.

(3) The method according to (2), wherein n is 2 and the compound is represented by the formula

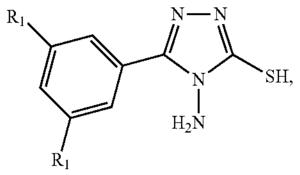

wherein each $R_1$ is independent of the other and represents a halogen atom selected from the group consisting of bromo, chloro, fluoro and iodo.

(4) The method according to any one of (1)-(3), wherein n is 2 and each R1 is the same and represents bromo, chloro or fluoro.

(5) The method according to (2), wherein n is 1 and R1 is selected from the group consisting of bromo, chloro and fluoro, provided that each R1 is not the same halogen.

(6) The method according to (1), wherein R1 represents fluoro when n is 1 and wherein R1 represents chloro when n is 2.

(7) The method according to (2), wherein the compound comprises at least one of the following:

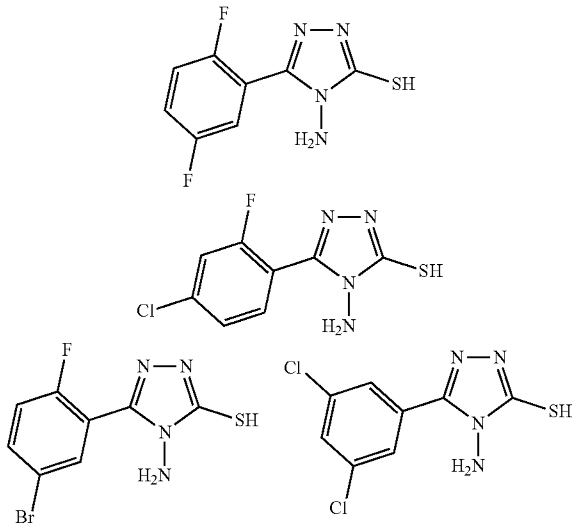

(8) The method according to any one of (1)-(7), wherein the virus is from the family Herpesviridae.

(9) The method according to (8), wherein the virus is HSV-1.

(10) The method according to any one of (1)-(8), wherein the combinatorial method includes administering, as the anti-viral drug, an anti-herpes drug.

(11) The method according to (10), wherein the anti-herpes drug comprises acyclovir, a pharmaceutically acceptable salt of acyclovir, or a combination thereof.

(12) The method according to any one of (1)-(9), wherein the combinatorial method includes administering, as the pro-drug, a pro-drug for an anti-herpes drug.

(13) The method according to (12), wherein the pro-drug for an anti-herpes drug comprises valacyclovir, a pharmaceutically acceptable salt of valacyclovir, or a combination thereof.

(14) A combinatorial method for inhibiting the replication of a virus that utilizes an internal ribosome entry site in its replication, comprising administering a compound, a tautomer, or a pharmaceutically acceptable salt or pharmaceutically acceptable ester thereof, in an amount effective for inhibiting replication of the virus in cells, wherein the compound is represented by the formula:

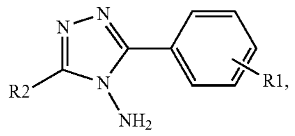

wherein R1 represents phenyl para-substituted with $C_1$-$C_6$ alkoxy, n is an integer of 1, 2, or 3, and R2 represents $—S—(CH_2)_n—COOH$; and either separately administering an anti-viral drug and/or pro-drug for the anti-viral drug or co-administering the anti-viral drug and/or the pro-drug with the compound, its pharmaceutically acceptable salt, or its pharmaceutically acceptable ester.

(15) The method according to (14), wherein the anti-viral drug comprises an anti-herpes drug.

(16) The method according to (14), wherein the anti-herpes drug comprises acyclovir, a pharmaceutically acceptable salt of acyclovir, or a combination thereof.

(17) The method according to (14), wherein the pro-drug comprises a pro-drug for an anti-herpes drug.

(18) The method according to (17), wherein the pro-drug valacyclovir, a pharmaceutically acceptable salt of valacyclovir, or a combination thereof.

(19) The method according to any one of claims (14)-(18), wherein R1 represents methoxy.

(20) The method according to any one of (13)-(19), wherein R2 represents $—S—(CH_2)—COOH$.

(21) The method according to (14), wherein the compound is represented by the formula:

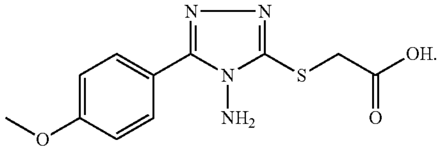 [SMILES: COc1ccc(-c2nnc(SCC(=O)O)n2N)cc1]

(22) The method according to any one of (1)-(7), wherein the virus is from the family Coronaviridae.

(23) The method according to (22), wherein the virus is SARS-CoV-2.

INCORPORATION BY REFERENCE

All patents, publications, and patent applications cited in the present specification are herein incorporated by reference as if each individual patent, publication, or patent application was specifically and individually indicated to be incorporated by reference in its entirety for all purposes.

DETAILED DESCRIPTION OF THE INVENTION

Figure 1:
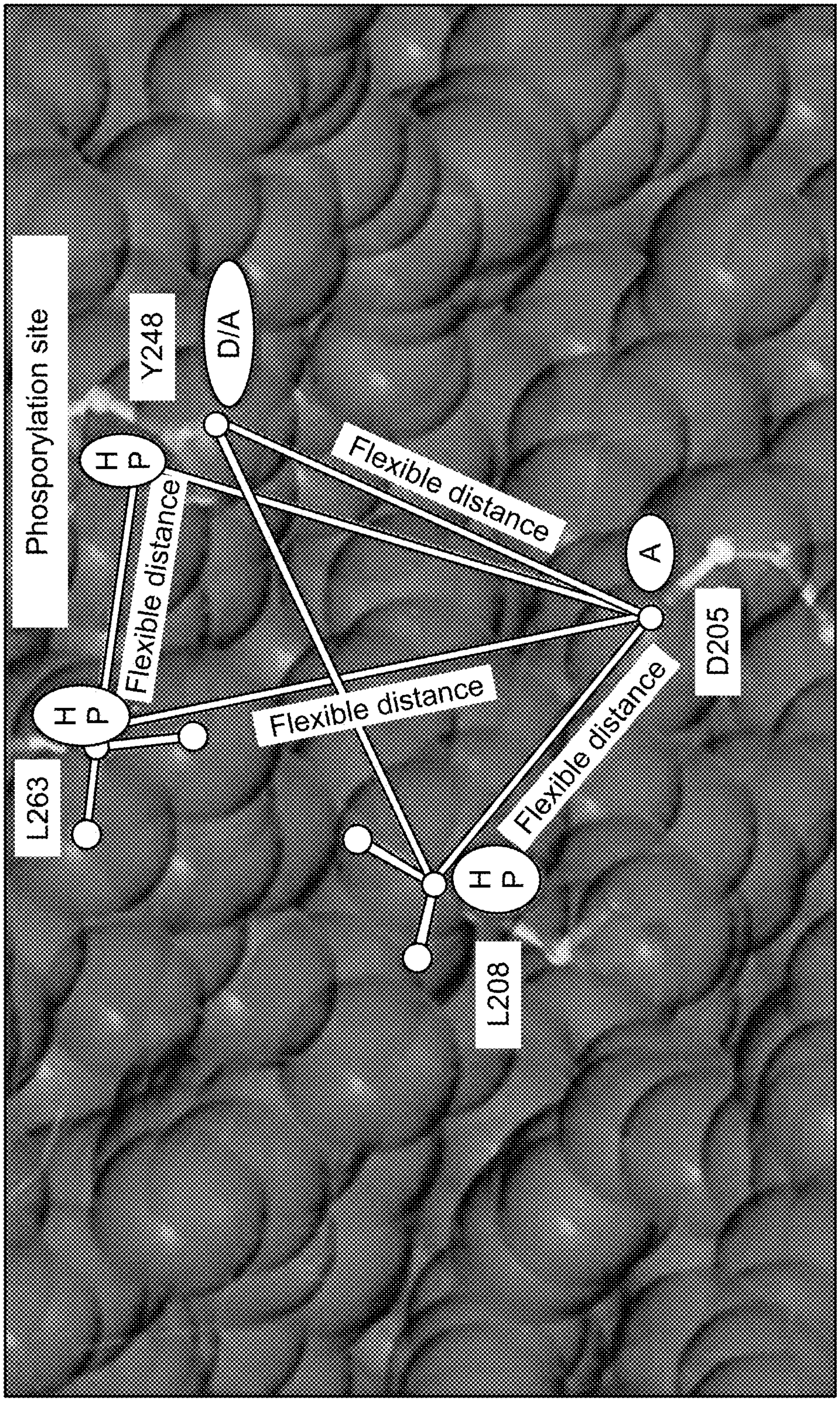
FIG. 1 shows sample two receptor-based three-point pharmacophore models generated on the RACK1A phosphorylation site with exclusion spheres colored pink, geometric and distance constraints (flexible) shown as lines, and filled white circles as centers. HP-hydrophobic; D-donor; A-acceptor.

In one aspect of the present disclosure, a method of treating, or at least inhibiting or suppressing, a viral infection from an IRES-utilizing virus (such as an IRES-utilizing virus from the family Herpesviridae or Coronaviridae) is disclosed. Embodiments of such a method may comprise administering a therapeutically effective amount of a compound, a tautomer thereof, or a pharmaceutically acceptable salt thereof.

In some embodiments, a combinatorial method for treating, or at least inhibiting or suppressing, an IRES-utilizing virus (such as an IRES-utilizing virus from the family Herpesviridae or Coronaviridae) in a host comprises administering a therapeutically effective amount of a compound, or a tautomer thereof, or a pharmaceutically accept salt thereof, capable of inhibiting or interfering with viral proliferation; and either administering another anti-viral drug and/or prodrug, or co-administering another anti-viral drug and/or pro-drug with the compound, its tautomer, or its pharmaceutically acceptable salt.

Example embodiments of the disclosed subject matter herein provide a method for treating against IRES-utilizing pathogenic viruses.

Representative species of IRES-utilizing viruses have been identified via suitable software, such as the IRESPred software, as described in Kolekar et al., IRESPred: Web Server for Prediction of Cellular and Viral Internal Ribosome Entry Site (IRES), Scientific Reports, 6:27436 (June 2016). IRESPred reported IRES-containing viruses including HIV-1, Herpes Simplex Virus (HSV), and Hepatitis viruses to have IRES in their 5'UTR (Untranslated Region). Replication/proliferation of these IRES-utilizing viruses in a host via IRES-mediated translation of their viral mRNA can be inhibited by a present method.

IRES-containing viruses requiring IRES-dependent translation that can be treated against by a present method include viruses in the Flaviviridae family of viruses, viruses in the Picornaviridae family of viruses, viruses in the Poxviridae family of viruses, viruses in the Herpesviridae family of viruses, and viruses in the Coronaviridae family of viruses, by way of examples. The Flaviviridae family of viruses includes Hepatitis C, Zika virus, West Nile Virus, and Dengue virus. IRES-containing viruses, such as Hepatitis C (HCV) and Dengue Virus NS1 require host RACK1 protein for IRES-mediated translation of virial mRNA. *Cell,* 159 (5):1086-1095 (2014) (Hepatitis C); Cell Reports, 21(13): 3900-3913 (Dec. 26, 2017) (Dengue Virus NS1). HCV is a positive strand RNA virus dependent on a highly structured IRES for its translation. The Picornaviridae family of viruses include the enteroviruses, such as Enterovirus D68 among others, apathoviruses, cardioviruses and hepatoviruses, among others. The Picornaviridae family of viruses is described in Current Pharmaceutical Design, 10:3757-3767 (2004). Enteroviruses, such as EV-D68, are described in AnnalsATS, 12(5):775-781 (2015); and Science, 347(6217): 71-74 (2017). The Poxviridae family of viruses include the Vaccina (Vac V) virus as an example. The Herpesviridae family of viruses includes Herpes Simplex Virus (e.g., HSV-1 and HSV-2). The Coronaviridae family of viruses includes 229E (an alpha coronavirus); NL63 (an alpha coronavirus); OC43 (a beta coronavirus); HKU1 (a beta coronavirus); MERS-CoV (the beta coronavirus that causes Middle East Respiratory Syndrome, or MERS); SARS-CoV (the beta coronavirus that causes severe acute respiratory syndrome, or SARS); and SARS-CoV-2 (the novel coronavirus that causes coronavirus disease 2019, or COVID-19). Additionally, IRES-containing viruses requiring IRES-dependent translation that can be treated against by a present method may further include plant viruses, including plant RNA viruses. Such plant viruses may include, for example, crucifer-infecting tobamovirus (CrTMV), turnip crinkle virus (TCV), and *Pelargonium* flower break virus (PFBV). Hence, the methods and compounds herein may be used to inhibit plant viruses, and to thereby reduce yield losses caused by plant viral diseases.

Representative IRES-utilizing viruses include, for example, HSV-1, and SARS-CoV-2.

A herpesvirus is an example of an internal ribosome entry site (IRES)-containing virus, and the latter refers to a virus requiring a host's receptor for Activated C Kinase 1

(RACK1) protein to interact with the viral IRES for viral mRNA translation. RACK1 is a specific host factor required for IRES-mediated translation by such viruses. Thus, without being restricted thereto, it is believed the compound(s), its tautomer(s), or its pharmaceutical salts interfere with the host's RACK1, thereby blocking its interaction with the viral mRNA of an IRES-utilizing virus required for IRES-dependent viral replication, and thus stopping viral proliferation.

A combinatorial method for treating, or at least inhibiting or suppressing, such a virus includes treating a host infected with such virus with an amount of one or more compounds, tautomers thereof, or pharmaceutically acceptable salts thereof, effective for interfering with replication of the internal ribosome entry site utilizing virus (IRES-utilizing virus) in the host.

The combinatorial treatment includes administering the compound(s), its tautomer(s), and/or its pharmaceutical salts to the host. In one of its aspects the compound is represented by the formula (1):

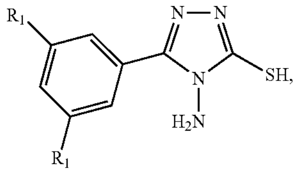

wherein each $R_1$ is independent of the other and each represents a halogen atom. Accordingly, in an aspect of a combinatorial method for treating, inhibiting or suppressing an IRES-utilizing virus, each $R_1$ independent of the other represents a halogen atom selected from the group consisting of bromo, chloro, fluoro and iodo.

In an aspect of a combinatorial method, a compound represented by formula (2), which is an example of a compound represented by formula (1), a tautomer thereof, or a pharmaceutically acceptable salt thereof, is administered to a host in need of treatment to at least effect inhibition or suppression, if not block, replication of a IRES-utilizing virus:

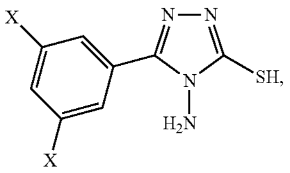

wherein each X is the same and represents a halogen atom (bromo, chloro, fluoro, or iodo).

It will be appreciated that an administration can be to a host that is a patient in need of treatment or to cells.

A compound, denoted SD-29-14, its tautomer or a pharmaceutically acceptable salt is illustrative of formulas (1) and (2). This compound is represented by formula (3) below:

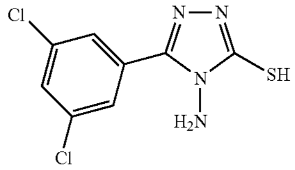 [SMILES: Nn1c(S)nnc1-c1cc(Cl)cc(Cl)c1]

The compounds of formula (1), (2) and (3) are capable of treating against, or at least inhibiting or suppressing, viral replication (proliferation) of an IRES-utilizing virus (such as a herpesvirus).

It is preferred that in a present combinatorial method the compound exhibits comparatively lower relative cell toxicity while exhibiting effectiveness in treating against the IRES-utilizing virus.

In a compound represented by various of the formulae herein, such as formulae (1), (2) and (3), by preference the azole moiety is shown with an —SH substituent and it will be appreciated tautomers in which there is a ═S moiety instead may be used. So too for a compound represented by any of formulas (4) and (5).

Pharmaceutically acceptable excipients and salts are described in Remington, The Science and Practice of Pharmacy, $20^{th}$ Edition (2000). Salts are described at pages 703-711. A hydrohalide, such as a hydrochloride of a compound herein is an example.

The "anti-viral drug" is by preference one having a different mode of action than a compound represented by a formulae herein. An anti-herpes drug includes, by way of example, acyclovir, a pharmaceutically acceptable salt of acyclovir or a combination thereof. The "pro-drug" is by preference one that undergoes in vivo conversion to an "anti-viral drug." A pro-drug includes, by way of example, valacyclovir, a pharmaceutically acceptable salt of valacyclovir, or a combination thereof. By preference, in the combinatorial treatment the amount of the anti-viral drug and/or pro-drug is an amount sufficient to exhibit anti-viral action, e.g., in some therapeutically effective amount. In principle, for an anti-viral drug or pro-drug having regulatory approval, the approved dosage may also be considered for use in a combinatorial treatment.

In some aspects, a combinatorial method for treatment disclosed herein unexpectedly shows at least a marked impairment (inhibition/suppression) of viral replication of mRNA (e.g., non-capped mRNA) for an IRES-utilizing virus. Such IRES-utilizing viruses require a host ribosomal protein known as RACK1 for IRES-mediated translation (replication) of viral mRNA, and disclosed methods herein provide a treatment that interferes with the host RACK1 protein to thereby block IRES-mediated translation of the viral mRNA in IRES-utilizing viruses.

A compound represented by a formulae herein functions as a RACK1 inhibitor. A related method therefor comprises administering an amount of a compound of a formulae herein, such as any of formulae (1), (2), (3), or (4) by way of example, or a tautomer or a pharmaceutically acceptable salt thereof, in an amount effective for inhibiting a host's RACK1 protein. Target sites, such as sites the Y248 site (in *Arabidopsis*) and/or similar sites in human RACK1 (e.g., Y246 in human RACK1), and/or other sites, such as the so-called K273 pocket and similar site(s) in human RACK1, may be involved. A RACK1 inhibitor interferes with the site(s) (sometimes called pocket(s)) in the RACK1 of interest, such as human RACK 1, so that the RACK 1 as modified by a compound of a formulae herein is inhibited.

A compound represented by a formula herein exhibits an improvement in stopping, or at least inhibiting or suppressing or stalling, viral replication of an IRES-utilizing virus which involves disrupting the interaction of a host RACK1 protein with the viral IRES required for IRES-mediated translation of viral mRNA (e.g., uncapped viral mRNA).

Certain compound(s) represented by a formula herein exhibit an improvement in inhibiting viral replication of an IRES-utilizing virus (e.g., a herpesvirus or a coronavirus) as compared to a compound (SD-29) in which the phenyl ring is mono-substituted (fluoro) at the para-position.

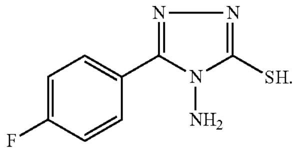 [SMILES: Nn1c(S)nnc1-c1ccc(F)cc1]

Data show the efficacy using the SD-29-14 compound alone for treating against viral IRES-mediated translation as in an IRES-utilizing virus, such as HSV-1, starts in vitro at a lower concentration, such as at 1 μM (which is 100 times better than that of a SD-29 compound), and in a dose dependent way, and is effective in at least inhibiting, suppressing or stalling, HSV-1 proliferation. This is supported, for example, from data obtained using a Luciferase signal as the measurement of HSV-1 proliferation (as the virus is tagged with the luciferase signal producing tag).

Certain compound(s) represented by a formula herein may exhibit an improvement in inhibiting viral replication of an IRES-utilizing virus from the Herpesviridae family of viruses as compared to others of the compound(s) described.

Herpesviruses are among the diverse viruses that utilize a host protein, known as Receptor for Activated Kinase 1 (RACK1), to translate mRNAs using a secondary structure known as the Internal Ribosome Entry Site (IRES). In other words, RACK1 plays an essential role in the IRES-dependent translation of the mRNA of such viruses. In a method using a compound described herein, the compound can target and bind to the RACK1 functional site(s) in the host's RACK1 to produce modified RACK1, such as to increase instability of the RACK1 protein. In principle, depletion of modified RACK1 from the host cell (as supported by data from Western assay(s)), can be the potential mechanism (as without the RACK1 in the ribosome, IRES-containing viruses would not be able to replicate their mRNAs (e.g., non-capped mRNA)).

A present method in one of its aspects is a method for treating against IRES-utilizing pathogenic viruses such as a herpesvirus or a coronavirus.

Representative species of IRES-utilizing viruses have been identified via suitable software, such as the IRESPred software, as described in Kolekar et al. (IRESPred: Web Server for Prediction of Cellular and Viral Internal Ribosome Entry Site (IRES), *Scientific Reports,* 2016, 6:27436). IRESPred reported IRES-containing viruses including HIV-1 and Herpes Simplex Virus (HSV) to have IRES in their 5'UTR (Untranslated Region). Thus HIV, including HIV-1, may be an IRES-utilizing virus of the present disclosure.

Replication/proliferation of these IRES-utilizing viruses in a host via IRES-mediated translation of their viral mRNA can be inhibited by a method disclosed herein.

Exemplary IRES-containing viruses requiring IRES-dependent translation that can be treated against by a present method include viruses in the Herpesviridae family of viruses, which includes Herpes Simplex Virus (e.g., HSV-1 and HSV-2); and viruses in the Coronaviridae family of viruses, which includes SARS-CoV-2.

Though many coronavirus proteins are synthesized by a cap-dependent mechanism, reports indicate that a cap-independent IRES-based translation mechanism is utilized by several coronavirus mRNAs. Nakagawa K, Lokugamage K G, Makino S ("Viral and Cellular mRNA Translation in Coronavirus-Infected Cells," *Adv. Virus Res.,* 2016, 96:165-192). It has been reported that mRNA 3 of infectious bronchitis virus (IBV) from the sub-genomic RNA is functionally tricistronic, having the capacity to encode three proteins (3a, 3b, and 3c) from three ORFs, with 3c translation initiation depending on upstream 3a/b sequences that serve as an IRES element. Liu D X, Inglis S C ("Internal entry of ribosomes on a tricistronic mRNA encoded by infectious bronchitis virus," *J. Virol.,* 1992, 66:6143-6154). Further analyses showed that the sequence prior to the initiator AUG of 3c can form an RNA secondary structure comprised of five RNA stem-loops that can be modeled into a compact superstructure formed by interactions of two predicted pseudoknot structures.

IRES-mediated translation was also reported in the coronavirus MHV (mouse hepatitis virus). The unique region of MHV mRNA 5 has two ORFs: ORF 5a and ORF 5b. Thiel and Siddell reported that a synthetic mRNA containing both ORFs is functionally bicistronic; and that expression of ORF 5b, but not ORF 5a, is maintained in a tricistronic mRNA containing an additional 5'-proximal ORF. These data suggested that initiation of protein synthesis from ORF 5b may be mediated by an internal entry of ribosomes. Thiel V, Siddell S ("Internal ribosome entry in the coding region of murine hepatitis virus mRNA 5," *J. Gen Virol.,* 1994, 75:3041-3046). Jendrach et al. then identified the IRES element which contains ≤280 nucleotides including the ORF 5b initiation codon. Jendrach M, Thiel V, Siddell S ("Characterization of an internal ribosome entry site within mRNA 5 of murine hepatitis virus," *Arch. Virol.,* 1999, 144:921-933).

The present inventors have identified SARS-CoV-2 as a putative IRES-utilizing virus treatable by the disclosed methods herein. By analyzing the genome sequence of SARS-CoV-2, the present inventors have discerned that many of its mRNAs mainly on the sub-genomic RNAs—mRNA7b, mRNA9b, mRNA14, and ORF10—may be translated through a cap-independent mechanism, such as through IRES-based translation. Wu et al. identified several translational regulatory sequences (TRS) in the genomic sequences of SARS-CoV-2, Wu et al. ("A new coronavirus associated with human respiratory disease in China," *Nature,* 2020, 579(7798):265-269), and these could potentially aid in the translation of the downstream ORF in a cap-independent manner. Typically, upstream ORFs suppress translation of their associated downstream coding regions under normal growth conditions. However, under cellular stresses, the suppression by upstream ORFs is released, and thus translation of the downstream ORFs can be activated/increased. This phenomenon has been documented in numerous positive-sense single-stranded viruses. Yang et al. ("IRES-mediated cap-independent translation, a path leading to hidden proteome," *Journal of Molecular Cell Biology*, Volume 11, Issue 10, October 2019, Pages 911-919). Moreover, IRESs can also enhance the repertoire of the synthesized proteins from a single transcript. They enable the production of a protein from an independent open reading frame (ORF) in a bicistronic transcript, similar to the ones identified within the SARS-CoV-2 genome, and guide the ribosome to produce an N-truncated isoform from an alternative AUG located downstream to the authentic start codon.

Thus, TRS sequences within the SARS-COV-2 genome have the potential to function as an IRES, to aid in the cap-independent translation of the downstream ORF within a bicistronic ORF in a cap-independent manner. There are several bicistronic ORFs present within the SARS-COV-2 genome. Also, further supporting the present inventor's identification of SARS-COV-2 as a putative IRES-utilizing virus treatable by the disclosed methods herein, closely related CoV-HKU1 maintains a stretch of 13 nucleotides, AUUUAUUGUUUGG (SEQ ID NO: 6), which is similar to the IRES element, UUUUAUUCUUUUU (SEQ ID NO: 7), in MHV, upstream of the initiation codon of the E protein. A similar sequence is also present at a similar position of the SARS-COV-2 genome sequence. Wu et al. ("A new coronavirus associated with human respiratory disease in China," *Nature,* 2020, 579 (7798): 265-269).

The present inventors envision that compounds of the present disclosure may be effective in treating, or at least inhibiting or suppressing, SARS-CoV-2 by inhibiting the interaction of RACK1 with Host Annexin A2 (ANXA2). ANXA2 has been found to bind the coronavirus IBV (Infectious Bronchitis Virus) pseudoknot RNA, to regulate the frameshifting efficiency of the virus; and overexpression of ANXA2 significantly reduced the frameshifting efficiency from IBV pseudoknot RNA, whereas knockdown of the protein strikingly increased the frameshifting efficiency. Kwak H, Park M W, Jeong S ("Annexin A2 Binds RNA and Reduces the Frameshifting Efficiency of Infectious Bronchitis Virus," *PLoS ONE,* 2011, 6(8):e24067). RACK1 has been found to interact with ANXA2, Nilsson J, Sengupta J, Frank J, Nissen P ("Regulation of eukaryotic translation by the RACK1 protein: a platform for signaling molecules on the ribosome," 2004, EMBO Rep 5: 1137-1141).

Without being bound by a particular theory, the present inventors believe that compounds of the present disclosure may be used in treating, or at least inhibiting or suppressing, SARS-CoV-2, by inhibiting this interaction between RACK1 and ANXA2 (so as to allow the overexpression of (free) ANXA2 to inhibit frameshifting in SARS-CoV-2). As SARS-CoV-2 efficiently uses frameshifting to produce the 1ab polyprotein that gives rise to all of the nsp1-nsp16 proteins, the present inventors envision that the application of the RACK1 inhibitor compounds of the present disclosure will inhibit frameshifting by resulting in the generation of excess free ANXA2, which may inhibit frameshifting by binding to the pseudoknot structure just upstream of the frameshifting site.

In addition, in many cases viral infection causes an increase in both ribosome biogenesis and the synthesis of ribosomal proteins after the inhibition of host mRNA translation. Simonin, D., Diaz, J. J., Masse, T., Madjar, J. J ("Persistence of ribosomal protein synthesis after infection of HeLa cells by herpes simplex virus type 1," *J. Gen. Virol.,* 1997, 78, 435-443). Coronaviruses have been found to exemplify this process of increased ribosome and ribosomal protein biogenesis. For instance, the N protein of Avian infectious bronchitis coronavirus (AIBV) localizes to the nucleolus in a cell cycle dependent manner and interacts with fibrillarin and nucleolin, which are two major components of the nucleolus involved in ribosome biogenesis. Cawood, R., Harrison, S. M., Dove, B. K., Reed, M. L., Hiscox, J. A ("Cell cycle dependent nucleolar localization of the coronavirus nucleocapsid protein," Cell Cycle, 2007, 6:863-867). RACK1 protein is a known ribosomal scaffolding protein that is also required for viral IRES-mediated translation through the association with eIF3 to assemble a translation preinitiation complex. Majzoub K, Hafirassou M L, Meignin C, Goto A, Marzi S, Fedorova A, Verdier Y, Vinh J, Hoffmann J A, Martin F, Baumert T F, Schuster C, Imler J L ("RACK1 controls IRES-mediated translation of viruses," *Cell,* 2014; 159:1086-95). As most of the IRES-based translation requires host diverse initiation factors and increased biogenesis of ribosomes and ribosomal proteins, RACK1 places itself in the regulatory position to mediate the viral mRNA translation. Compounds of the present disclosure may therefore be used to inhibit the functionality of RACK1 protein; and the unavailability of RACK1 protein to mediate viral mRNA translation may thereby inhibit coronavirus replication, including SARS-CoV-2.

Figure 18:
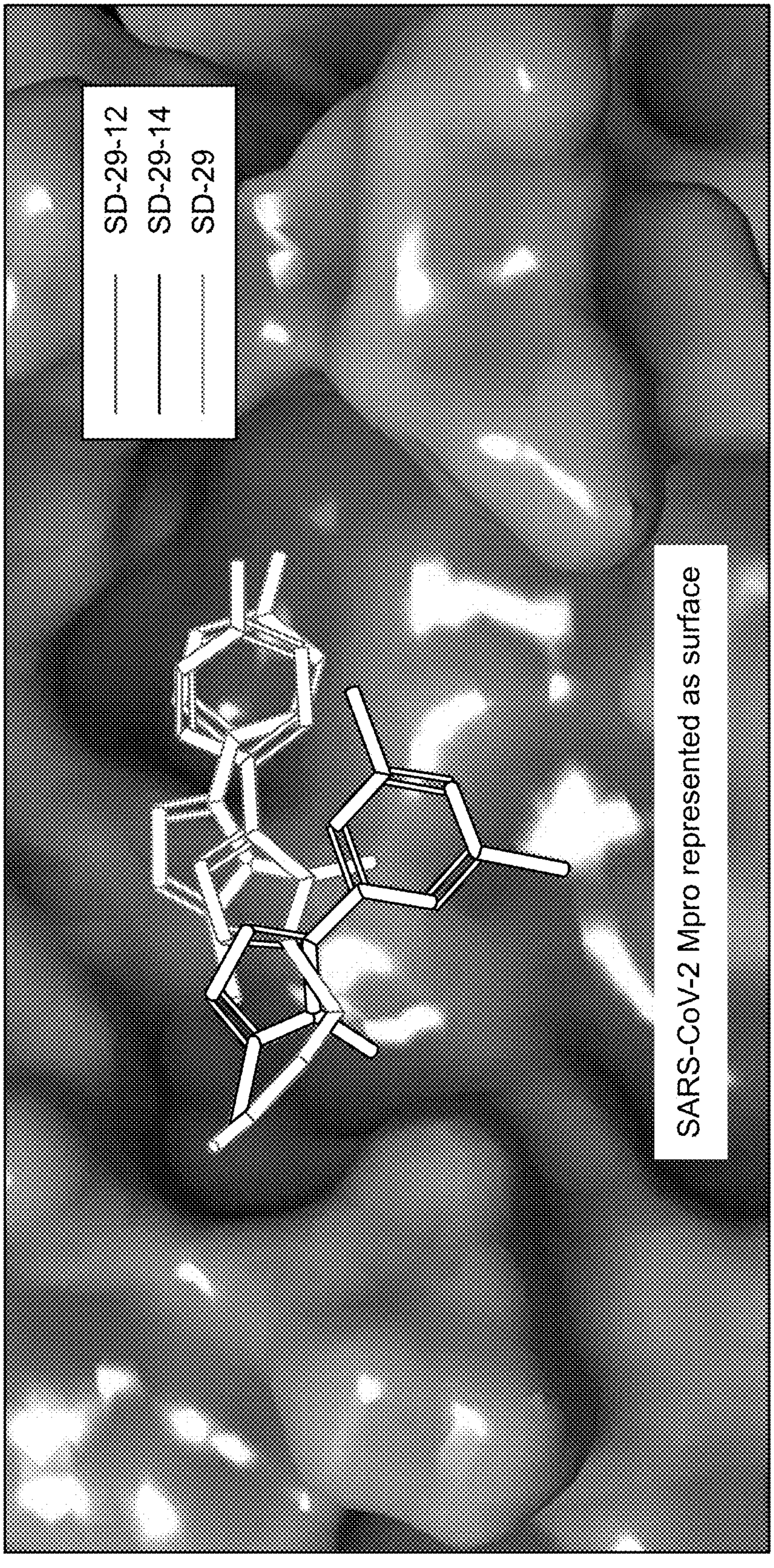
FIG. 18 shows a predicted structural model of SD-29, SD-29-12 and SD-29-14 binding to SARS-CoV-2 Mpro.

Additionally, based on additional bioinformatic analyses (data not shown), the present inventors consider that several of the RACK1 inhibitor compounds of the present disclosure may exert their inhibitory effect by directly binding to SARS-CoV-2 proteins, thereby inhibiting the function of those proteins. For example, SD compounds have been identified in silico as potential inhibitors of SARS-CoV-2 Main Protease Mpro or 3CLpro protein. The predicted structural model of SD-29, SD-29-12 and SD-29-14 binding to Mpro is shown in FIG. 18.

Data show that a compound(s) described herein disrupts or interferes with a host RACK1 protein (e.g., in yielding modified RACK1). Data show such compound(s) can be administered to at least inhibit proliferation/replication of IRES-dependent viruses. RACK1 mediated translation is a critical step in virus propagation for IRES-dependent viruses. Impairing RACK1 can therefore lead to blocking or inhibiting or suppressing such IRES-utilizing viruses. Data from in vitro testing indicate the compound(s) are able to inhibit IRES activities in representative IRES-utilizing viruses from the Herpesviridae family of viruses, such as HSV-1, by way of example.

In embodiments of the present disclosure, a host may be in need of treatment (because, for example, they are infected with an IRES-utilizing virus). The host may comprise cells in a mammal (patient, e.g., human) in need of treatment. It will also be appreciated that the method can be practiced with cells in vivo or in vitro.

Compounds in accordance with a formula herein can be prepared by adapting the following synthesis.

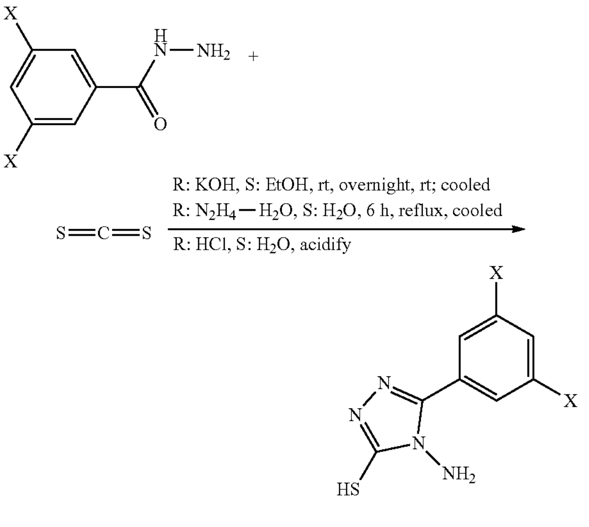

Each X, independent of the other, represents a halogen atom.

An exemplary method for synthesizing a compound known as SD-29-14 is:

SD-29-14

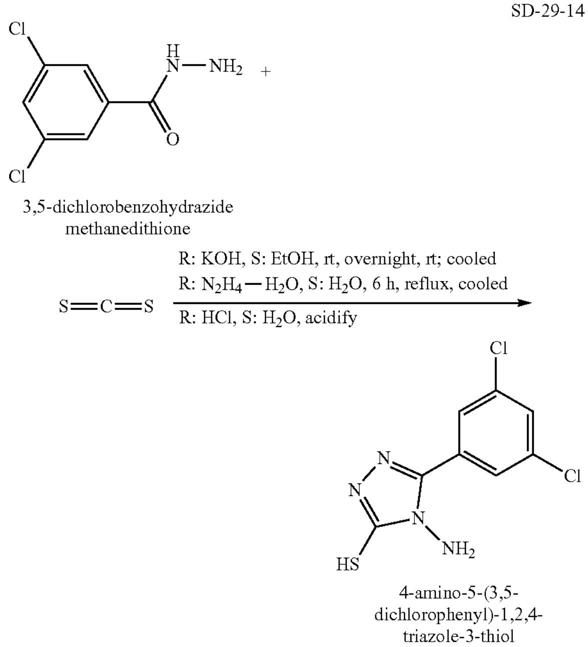

3,5-dichlorobenzohydrazide methanedithione 4-amino-5-(3,5-dichlorophenyl)-1,2,4-triazole-3-thiol Other syntheses can be adapted from Molecules, 6:815-824 (2001); Sung et al. (*J. Heterocyclic Chem.,* 29:1101-1109 (2012)); *Int'l. J. Innov. Res. and Create. Tech.,* 1(1): 82-87 (2015).

Compounds of a formula herein, such as formulas (1)-(3), can also be synthesized by adapting the following synthesis. The hydrazide (0.04 mol) and KOH (0.04 mol) in 50 $cm^3$ MeOH is treated with $CS_2$(0.04 mol), and the mixture is stirred for 16 h at room temperature. Diethyl ether (50 $cm^3$) is added, and the precipitated solid is filtered, washed with ether, and vacuum-dried at 78° C. in a drying pestle. The potassium salts of substituted dithiocarbazinic acids are used for the next step without further purification. The potassium salt of the substituted dithiocarbazinic acid (0.02 mol) and hydrazine hydrate (0.04 mol) in 2.0 $cm^3$ water are heated under reflux with stirring for 0.5-1.5 h. The color of the reaction mixture changes to green with the evolution of hydrogen sulfide, and a homogeneous solution is formed in about a half an hour. When evolution of hydrogen sulfide ceases (lead acetate test), the reaction mixture is diluted with 50 $cm^3$ cold water and acidified with 6 N hydrochloric acid. The precipitated solid was filtered, washed with cold water, and recrystallized from aqueous EtOH.

A general discussion of determining the effect of inhibition of IRES-mediated translation appears in Plank et al., *Nucleic Acids Research* 41(13):6698-6714 (2013).

The expression of a protein within the viral genome can be assessed by diverse means. For example, the tagged protein may exhibit luminescence or fluorescence so as to permit the amount of expression to be determined by the amount of light given off by the culture and/or a lysate thereof. In combination or in the alternative, the expression of a protein may be determined by the binding of various markers, such as antibodies, for proteins within the viral genome. Other means known to those skilled in the art of detecting the presence or absence of a protein within a viral genome following infection of cell culture may also be used.

Regardless of the manner in which expression of protein within a viral genome is assessed, diminished amounts of the assessed protein in infected cultures treated with a compound in accordance with any of the formulae herein, or a pharmaceutically acceptable salt thereof, compared to identically infected cultures not treated with the compound or its salt, evidences the capacity of the compound and/or its salt to inhibit expression of at least a portion of a virus genome containing an IRES sequence.

Assessing the expression of an introduced protein may enable an assessment of viral proliferation by means not normally permitted by the native viral genome. For example, proliferation of an IRES-containing virus treated (e.g., inhibited or suppressed) by a present method, can be assessed using luminescence. Accordingly, proliferation of a luminescence-modified virus will entail production of the luciferase protein. As the luciferase protein causes fireflies to glow, production of the luciferase protein by infected cells as a result of viral proliferation will enable infected cells actively producing the luminescence-modified virus to glow. However, if cells infected with the IRES-containing virus modified for luminescence do not glow when administered a compound in accordance with a formulae herein, or a pharmaceutically acceptable salt thereof, or a tautomer thereof, then the compound, its tautomer, or its salt, is capable of inhibiting expression of at least a portion of the viral genome containing an IRES sequence. Inhibiting expression of at least a portion of the viral genome means the compound would inhibit proliferation of the virus.

Figure 11A:
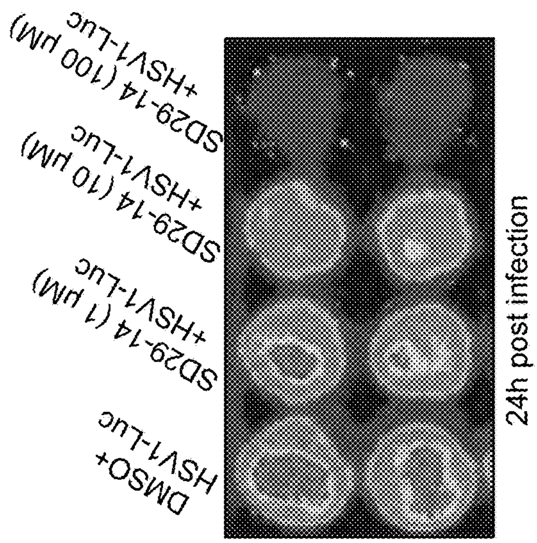
FIG. 11 shows visualization of the RACK1 inhibitor induced inhibition of HSV-1 proliferation in HEp-2 cells. The virus used in this diagram is an HSV-1 F strain expressing luciferase (R8411 mutant) under the control of the ICP27 promoter, and was a gift from Prof. Bernard Roizman (University of Chicago). HEp-2 cells were grown to 80-90% confluency in Dulbecco's Modified Eagle's medium (DMEM) supplemented with 10% fetal calf serum (PCS) and 1% penicillin-streptomycin (PS) and fungicide. The HSV-1 virus and the indicated concentration of compound(s) were added and incubated for 24 h (in panels A and B) and for 48 h (in panel C). The luciferase signals were imaged and quantified in a Perkin Elmer IVIS Spectrum Imaging system. Panel A shows luminescence (color imaging) 24 hours post-infection with Herpes Simplex Virus (HSV-1) for a representative compound within general formula (1) at different concentrations versus a control. High luminescence indicates high viral proliferation. The inhibitor compound(s) effectively inhibited the HSV-1 proliferation as can be seen in a dose dependent reduction in the luciferase signal (red). Panel B is a bar graph of a luciferase signal as shown in panel A for HSV-1 with no virus, virus treated with DMSO, and virus treated with different concentrations of a representative compound within general formula (1). Panel B shows quantification of the luciferase signal from the samples in panel A. Three replicates from two separate experiments were combined to generate the average and the standard error bar. Panel C depicts RACK 1 protein expression after 48 hours in the similar samples as depicted in panel A. Panel C shows that the inhibitor compounds reduce the RACK1 phosphorylated bands (higher than the 37 kD RACK1 size). The compound(s) inhibit Y248 phosphorylation of RACK1 protein.
Figure 11B:
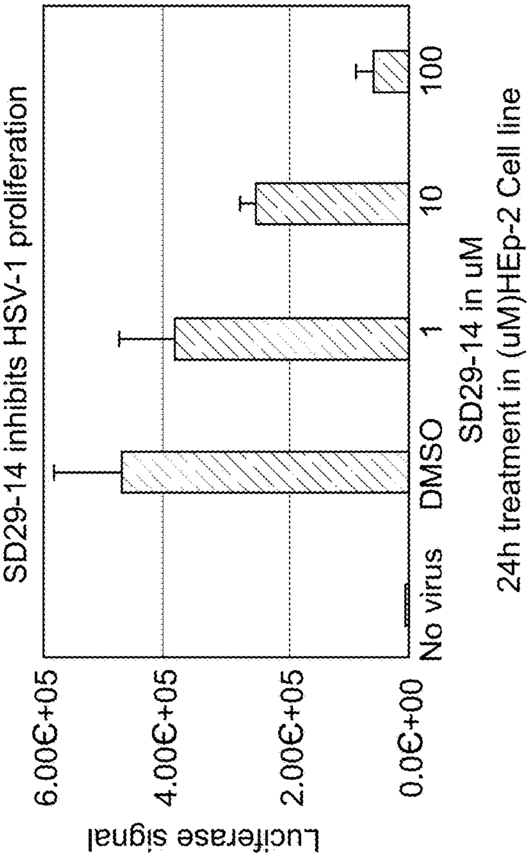
Figure 11C:
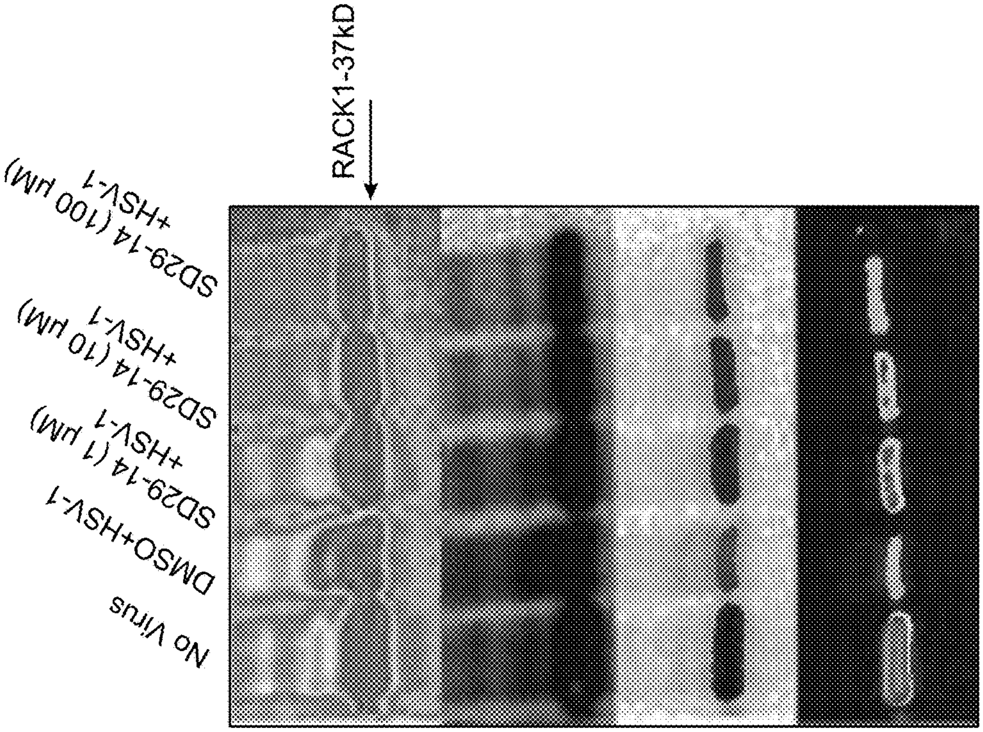

Visualization of the RACK1 inhibitor induced inhibition of IRES-containing viruses is illustrated as follows using HSV-1 proliferation in HEp-2 cells as an example. As an IRES-containing virus, an HSV-1 F strain expressing luciferase (R8411 mutant) under the control of the ICP27 promoter can be used. HEp-2 cells are grown to 80-90% confluency in Dulbecco's Modified Eagle's medium (DMEM) supplemented with 10% fetal calf serum (FCS) and 1% penicillin-streptomycin (PS) and fungicide. The HSV-1 virus and a concentration of an inhibitor compound(s) of a formulae herein are added and are incubated for 24 h and for 48 h (FIG. 11). The luciferase signals are imaged and are quantified in an imaging system, such as a Perkin Elmer IVIS Spectrum Imaging system. Inhibition against proliferation will be seen in a reduction in the luciferase signal.

Or, stated differently, visualization of RACK1 inhibitor induced inhibition of IRES-containing viruses is illustrated by the following protocol. To 80-90% confluent HEp-2 cells, HSV1-Luc (R8411) is added at a concentration of $2\times10^6$ pfu/ml along with indicated concentration of inhibitor compounds. After the described incubation period, luciferase activity is evaluated from bioluminescence images acquired by a Perkin Elmer IVIS Spectrum Imaging system immediately after adding luciferase substrate (D-luciferin, Gold Bio Technology) at a concentration of 400 μg/mL in medium. Bioluminescence intensity in different wells is quantified in units of photons per second per centimeter squared per steradian (p/s/$cm^2$/sr) by drawing a polygonal region of interest over the signals in images using Living Image 3.0 software (Caliper Life Sciences).

RACK1 regulation of IRES-mediated translation in HEp2 cells transformed with IRES plasmids can be detected using dual-luciferase reporter constructs. Gendron et al. (*Nucleic Acids Research,* 2011, 39(3):901-911). Dual-luciferase reporter constructs can be used to determine if the drug (compound(s)) targets IRES-mediated translation. For instance, IRES activity can be measured by calculating the ratio of FLUC to RLUC light production (RLUs) (Plank et al., *Nucleic Acids Research,* 2013, 41(13):6698-6714). RLAC is an acronym that refers to *Renilla* luciferase. FLUC is an acronym that refers to firefly luciferase.

Another technique for determining RACK1 inhibitor induced inhibition of an IRES-utilizing virus (e.g., a virus from the Herpesviridae or Coronaviridae families of viruses) comprises the Western assay. A Western assay technique can confirm that a compound of a formula herein is effective in stopping, if not inhibiting or suppressing or stalling, viral IRES-mediated translation of viral mRNA. For instance, this is seen from data that is obtained for HSV-1 virus described herein.

That is, in embodiments of the present disclosure, while the compounds of a formulae herein may be said to be anti-virals insomuch as they function as RACK1 inhibitors, for present purposes it will be appreciated that in the combinatorial treatments the anti-viral drug, and the pro-drug of an anti-viral drug, preferably differ in their mode of action from a compound of a formulae herein.

A RACK1 inhibitor composition, such as for a virus from the Herpesviridae or Coronaviridae families of viruses, can comprise a present compound, a tautomer thereof, or a pharmaceutically acceptable salt thereof, or an ester thereof, depending on the compound, and can additionally include a carrier suitable for the selected method of administration. For example, the RACK1 inhibitor can be formulated for enteral administration, such as in solid dosage form, such a capsule, tablet or the like, or can be formulated for parenteral administration, such as in a liquid suitable for administration orally or administration intravenously such as by injection. A present RACK1 inhibitor composition can be formulated for topical administration in treating against a herpesvirus. A RACK1 inhibitor formulation for administration to a host can also include an anti-viral drug, such as acyclovir, and/or a pro-anti-viral drug (sometimes referred to as a pro-drug for the anti-viral drug), such as valacyclovir.

Acyclovir can be administered orally, topically or parenterally, depending on the treatment and patient. Pharmaceutically acceptable salts of acyclovir can also be used, such as an alkali metal salt, e.g., acyclovir sodium, which can be used for the treatment of herpes simplex virus (HSV-1 and HSV-2) infections; the treatment of varicella-zoster infections in immunocompromised adults and children; the treatment of severe first episodes of genital herpes infections in immunocompetent individuals; and for the treatment of HSV encephalitis and neonatal HSV infections. In principle, a pro-drug can be used, such as valacyclovir as a pro-drug for acyclovir, as the anti-herpes drug in combinatorial application with our compounds. Valacyclovir includes pharmaceutically acceptable salts, such as valacyclovir hydrochloride that when administered orally, is rapidly absorbed from the GI tract and apparently nearly all converted to acyclovir, which in turn is converted in vivo to an active metabolite (acyclovir triphosphate) by viral thymidine kinase.

Another technique for assessing inhibition of viral infection by a compound or its pharmaceutically acceptable salt is by the broadly used and facile plaque assay technique. In general, in determining inhibition of viral replication, the cytopathic effect in the form of plaque formation over time is assessed by comparing virus-infected cells treated with a vehicle such as DMSO against virus-infected cells treated with the compound, a tautomer thereof or a pharmaceutically acceptable salt thereof.

A virus proliferating using an Internal Ribosome Entry Site (IRES) for viral mRNA translation may be referred to herein as an IRES-utilizing or IRES-containing virus. In other words, an internal ribosome entry site (IRES)-utilizing virus refers to a virus requiring a host's RACK1 protein to interact with the viral IRES for viral mRNA translation.

Based on the data herein, the compounds of a formulae herein, such as the compound SD 29-14, and their tautomers and pharmaceutically acceptable salts, can interfere with (impair) a host's RACK 1 protein by interfering with the functional site(s) of the RACK 1 protein in a host, and thus interfere with interaction between the functional RACK1 protein(s) of the host and the viral IRES (so as to interfere with the viral IRES-mediated translation of viral mRNA translation, thereby stopping, or at least inhibiting or suppressing or stalling, viral replication).

A comparison of the efficacy of a compound of Formulas (1), (2) and (3) (e.g., SD 29-14) versus a known anti-herpes drug was conducted, as discussed below. Acyclovir is the major anti-herpes drug on the market. The efficacy of SD 29-14 was evaluated in a two-fold manner in view of an existing anti-herpes drug acyclovir.

DETAILED DESCRIPTION OF EXEMPLARY EMBODIMENTS

Hereinafter, the present application will be described in further detail with reference to examples. The examples are merely provided to more fully describe the present application, and it will be apparent to those of ordinary skill in the art that the scope of the present application is not limited to the following examples.

Example 1: Inhibition of HSV-1 Proliferation

1. Materials and Methods

Tissue Culture and Viruses

HEp-2 cells (ATCC) were used for the infection of HSV-1. The cells were maintained in Dulbecco's Modified Eagle's medium (DMEM) supplemented with 10% fetal calf serum (FCS) and 1% penicillin-streptomycin (PS). Wild-type HSV-1 strain 17 was obtained from R.D. Everett and used previously.

Antibodies

The antibodies used for Western blot (WB) and immunofluorescence are listed below. A monoclonal antibody against tubulin (T-9026) was purchased from Sigma-Aldrich (St. Louis, MO, USA; 1:1000 for WB); polyclonal antibody against ICP8, and monoclonal antibodies against HSV ICP0, ICP4, RACK1 and gD were purchased from Santa Cruz Biotechnology, Inc. (Santa Cruz, CA, USA).

Purification of Viruses

Herpesviruses were amplified in Vero cells. The viral supernatant was centrifuged at 8000 g for 20 min to remove cell debris. The clarified medium was transferred into SW27/28 ultra-clear centrifuge tubes that were underlain with 7 mL of 20% sorbitol buffer (20% D-sorbitol, 50 mM Tris-HCl, pH 7.2, and 1 mM MgCl) and centrifuged at 55,000 g for 1 hour. The purified viral pellet was re-suspended in PBS. The HSV-1 F strain expressing luciferase (R8411) under the control of the ICP27 promoter was a gift from Bernard Roizman (University of Chicago), and was constructed using an HSV-1 bacterial artificial chromosome (BAC) system described in Horsburgh et al. ("Genetic manipulation of herpes simplex virus using bacterial artificial chromosomes," *Methods Enzymol.,* 1999; 306:337-52).

Bioluminescence Luciferase Assay

To 80-90% confluent HEp-2 cells, HSV1-Luc (R8411) was added at a concentration of $2\times10^6$ pfu/ml along with indicated concentration of inhibitor compounds. After the described incubation period, luciferase activity was evaluated from bioluminescence images acquired by a Perkin Elmer IVIS Spectrum Imaging system immediately after adding luciferase substrate (D-luciferin, Gold Bio Technology) at a concentration of 400 μg/mL in medium. Bioluminescence intensity in different wells was quantified in units of photons per second per centimeter squared per steradian (p/s/$cm^2$/sr) by drawing a polygonal region of interest over the signals in images using Living Image 3.0 software (Caliper Life Sciences).

Immunoblot Analysis

Proteins were separated by SDS-PAGE (25 μg loaded in each lane), transferred to nitrocellulose membranes (Amersham Inc., Piscataway, NJ, USA), and blocked with 5% nonfat milk for 60 min at room temperature. Membranes were incubated overnight at 4° C. with primary antibody, followed by incubation with a horseradish peroxidase-coupled secondary antibody and detection with enhanced chemiluminescence (Pierce, Rockford, IL, USA), according to standard methods. Membranes were stripped with stripping buffer (100 mM 2-mercaptoethanol, 2% SDS, 62.5 mM Tris-HCl, pH 6.8), washed with PBS-0.1% Tween-20, and used to detect additional proteins. For *Arabidopsis* lysates one-week old seedlings were treated with 10 uM of ABA in the presence/absence of the inhibitor compounds for 12 hours in a growth chamber (overnight) at 22° C. mostly in the dark. Lysates were isolated in lysis buffer (Cell Signaling, Danvers, MA) supplemented with plant protease inhibitor (Sigma-Aldrich), phosphatase inhibitor cocktail A and B (Santa Cruz Biotechnology, Dallas, TX), and N-Ethylamaleimide (Sigma-Aldrich, St. Louis, MO). Twenty five microgram of proteins were loaded on the BioRad's 4-12% precast Bis-Tris polyacrylamide gel, transferred to a nitrocellulose membrane and then blocked with 5% Bovine Serum Albumin (BSA) for one hour, washed and incubated with the an antibody (1:100 dilution) to detect phosphorylated Y248 residue of RACK1A protein which was raised using the epitope: FSPNR{pTYR}WLCAATEH (Genscript, Piscataway, NJ, USA) (SEQ ID NO: 5). To make it specific to RACK1A pY248, it was raised by adsorbing against the RACK1A non-phosphorylated antigen and to a peptide antigen with sequence FSPNRYWLCAATEN (SEQ ID NO: 5) specific for the *Arabidopsis* RACK1B and RACK1C proteins. A rabbit secondary antibody (1:5000) was used. BIORAD's Clarity ECL substrate was used to visualize the bands. For a loading control, the same membrane stripped in mild stripping buffer and then probed with an *Arabidopsis* Actin antibody (Sigma-Aldrich, St. Louis, MO) to show the loading control.

RNA Isolation and Real-Time RT-PCR

Following instructions of the manufacturers, total RNA was isolated using Tri Reagent® (Ambion, Inc., Austin, TX). To quantitatively examine the mRNA level of HSV-1 ICP0 from the infected cells, real-time RT-PCR was undertaken using the QuantiTect SYBR Green RT-PCR kit (QIAGEN, Valencia, CA). The primers for HSV-1 ICP0 were: forward-5'-CTGCGCTGCGACACCTT-3' (SEQ ID NO: 1) and reverse-5'-CAATTGCATCCAGGTTTTCATG-3' (SEQ ID NO: 2); and the primers for beta-actin (as control) were: forward-5'-GGTTCCGATGCCCTGAGGCTC-3' (SEQ ID NO: 3) and reverse-5'-ACTTGCGGTGCACGATGGAGG-3' (SEQ ID NO: 4). 1 μg of total RNA and 0.2 μM of sense and antisense primers (amplifying the RNA fragment in NS5 location) were used in a final 25 μl master mix volume. PCR reactions consisted of 50 cycles with the following optimal conditions: 94° C. for 20 s; 50° C. for 1 min; 72° C. for 30 s; and an optimized collection data step, 80° C. for 5 s. Fluorescence (captured at 80° C.) was determined to be absent from the signal generated by primer dimers. Data were collected and recorded by the BIORAD CFX Manager software. The relative quantity of the ICP0 transcripts at the indicated time points was normalized to the relative quantity of the reference gene actin at the same time points and then the $\log_{10}$ copy number of the normalized RNA transcripts were calculated and presented on a bar chart. A melting temperature curve analysis was obtained by measuring (after the amplification cycles) the fluorescence during a period of warming from 60° C. to 95° C.

Plaque Formation Unit (PFU) Assay

The viral plaque assay was performed as previously described (Tang et al. "Determination of minimum herpes simplex virus type 1 components necessary to localize transcriptionally active DNA to ND10," *J. Virol.* 2003; 77:5821-28), with slight modifications. The HSV-1 strain 17 was diluted serially in a volume of 1 mL. Then 300 ul of the virus was added onto confluent HEp-2 cell monolayers in 12-well plates; each dilution had 3 wells. After adsorption for 2 h, the medium was removed and the cells were washed twice with serum-free DMEM and overlaid with phenol-free DMEM containing 5% FCS, 0.5% low-melting point agarose (GIBCO), and 1% penicillin-streptomycin. The cells were incubated at 370 C for 48 hours. Neutral red was added on the agarose to stain the live cells. The plaques were counted and reported as pfu per mL. Mean pfu was determined after averaging the number of pfu from different dilutions. Student's 1-tests were used to statistically analyze differences between the groups; a p-value lower than 0.005 was used as the threshold for a significant difference.

Immunofluorescence and Confocal Microscopy

Hep-2 cells were grown to about 80% confluency in 12 well plate and the cells were co-infected with HSV-1 at an MOI of 1.0 for 30 h along with the indicated inhibitor compounds and control. The cells were fixed at room temperature with 4% paraformaldehyde-PBS for 15 minutes and then permeabilized at room temperature by 0.5% Triton X-100-PBS (pH 7.4) for 10 min. The cells were then washed 3× with Ice cold PBS. The cells were incubated with 1% BSA, 22.52 mg/mL glycine in PBST (PBS+0.1% Tween 20) for 30 min to block unspecific binding of the antibodies. The cells were incubated in the 1:500 diluted anti-ICP0 antibody in 1% BSA in PBST in a humidified chamber overnight at 4° C. The cells were washed three times in PBS, 5 min each wash and then incubated with the anti-mouse FITC conjugated secondary antibody in 1% BSA for 1 h at room temperature in the dark. After washing three times with PBST for 5 minutes each, the cells were mounted on slide using Prolong Slowfade Gold with DAPI (4=,6=-diamidino-2-phenylindole; Invitrogen), and confocal analysis was performed using Nikon CSU series Spinning Disk confocal microscope. Images were taken to show infected cells (green) and total viable cells (with DAPI stained nuclear DNA).

Fluorescence Cell Sort: Hep-2 cells were grown to about 80% confluency in T25 Cell culture flask and were co-infected with HSV-1 at a MOI of 1.0 for 24 h along with the indicated inhibitor compounds and control. After trypsinization, the cells were fixed in 4% paraformaldehyde-PBS. The cells were treated in the same method as described in the immunofluorescence and confocal microscopy method section. The labeled cells were counted in a Nexcelom Vision Cellometer equipped with Brightfield & 2 Fluorescence Channels Filter Set 101: Excitation/Emission Peak: 475 nm/535 nm and Filter Set 202: Excitation/Emission Peak:

525 nm/595 nm. The stained cell samples (20 μl) were pipetted into a Nexcelom counting chamber and inserted into the image cytometer. Bright-field and fluorescent images were then captured and analyzed at four different locations by the Cellometer image analysis software to directly determine the cell concentration of fluorescently labelled cells. The mean±standard error is reported from three replicates.

Surface Plasmon Resonance (SPR) Assay

To obtain in vitro confirmation of the binding of the isolated compounds to the purified RACK1 protein, the small compound SD-29 and its structural analog SD29-12 were evaluated for their binding potential with the recombinant RACK1A proteins using the Surface Plasmon Resonance (SPR) chip. SPR experiments were carried out with a Biacore T200 equipped with a CM5 sensor chip. Briefly, recombinant RACK1A cysteine-tagged protein was immobilized on flow cell (FC) 2 in HEPES buffered saline (10 mM Hepes, pH 7.4, and 150 mM NaCl, 3 mM CaCl2)) using a thiol-coupling kit according to the manufacturer's protocol, resulting in immobilization levels of 4580 response units (RU). FC1 was only activated and inactivated and used as a reference. SD-29 stock solution was diluted to a final concentration of 100, 75, 50, 25, 10 μM and 1 μM injected in 10 mM Hepes, 150 mM NaCl, 3 mM CaCl2, 1% DMSO, and 0.5% P20. Each injection was repeated three times for 60 s. FC1 signals were deducted from FC2 for background noise elimination. $KD_{50}$ is calculated by the equation: $KD_{50}$=kd/ka; kd—dissociation rate constant, ka—association rate constant.

Compound Screening

Structure-based screening of two million commercially available diverse compounds was used to screen for small molecules against the RACK1 Y248 phosphorylation site. The diverse set of compounds was preselected in terms of the molecular and topological properties of the RACK1 Y248 binding site. Generation of Receptor Grids for Docking: Grids were generated using Schrodinger's Glide module. Grid center points were determined from the centroid of each protein's cognate ligand. To obtain the centroid, the Cartesian coordinates for each atom in the ligand were extracted and the average for each dimension was taken. To determine the size of the grids, a trial-and-error approach to determine the smallest grid size that would allow for the re-docking of all reference ligands was undertaken. The largest reference ligand as the upper size limit was chosen and a grid size of 20 Å on each side was the minimum to allow for it to dock was found. Thus, the grid size for docking simulations was set at 20 Å. The in-silico screened compounds were rank ordered based on Glide XP scoring function and top 22 compounds were tested in-vitro. Initially, the compounds were screened on crystalized plant structure (PDB: 3DMO) (Ullah H, Scappini E L, Moon A F, Williams L V, Armstrong D L, Pedersen L C "Structure of a signal transduction regulator, RACK1, from *Arabidopsis thaliana," Protein Sci.,* 2008; 17:1771-80), and later human RACK1 crystal structure was deduced by another group (PDB: 4AOW). Strikingly, sequence and structure of the Y248 phosphorylation site and K273 sumoylation sites are 100% identical.

2. Results

Post-translational modifications such as tyrosine phosphorylation and protein sumoylation have been implicated in the regulation of RACK1 function in various organisms. Chang B Y, Chiang M, Cartwright C A ("The interaction of Src and RACK1 is enhanced by activation of protein kinase C and tyrosine phosphorylation of RACK1, *J. Biol. Chem.,* 2001, 276: 20346-56); Yang X J, Gregoire S ("A recurrent phospho-sumoyl switch in transcriptional repression and beyond," *Mol. Cell,* 2006; 23:779-86). Mutagenesis work has identified Tyr246 as a potential phosphorylation site and has suggested a correlation between enhanced tyrosine phosphorylation of RACK1 and binding of RACK1 to Src tyrosine kinase. Chang B Y, Chiang M, Cartwright C A ("The interaction of Src and RACK1 is enhanced by activation of protein kinase C and tyrosine phosphorylation of RACK1, *J. Biol. Chem.,* 2001, 276: 20346-56). In plants, tyrosine phosphorylation by dual-specificity serine/threonine/tyrosine kinase has been proposed. Rudrabhatla P, Reddy M M, Rajasekharan R. ("Genome-wide analysis and experimentation of plant serine/threonine/tyrosine-specific protein kinases," *Plant Mol. Biol.,* 2006; 60:293-319). The Y248 residue of *Arabidopsis* RACK1A protein is the conserved residue that corresponds to the human RACK1 Y246 site in a sequence alignment. Ullah H, Scappini E L, Moon A F, Williams L V, Armstrong D L, Pedersen L C ("Structure of a signal transduction regulator, RACK1, from *Arabidopsis thaliana," Protein Sci.,* 2008; 17:1771-80). The RACK1A crystal structure showed that the side chain of Tyr248 (Y248) in the RACK1A protein is located at the end of the loop connecting β-strands A and B of blade 6, and is fully exposed to the solvent making it easily accessible for modification. Ullah H, Scappini E L, Moon A F, Williams L V, Armstrong D L, Pedersen L C ("Structure of a signal transduction regulator, RACK1, from *Arabidopsis thaliana," Protein Sci.,* 2008; 17:1771-80). Recently, it was shown that mutagenesis of Y248F abolished the homo-dimerization potential of RACK1A proteins. Kundu N, Dozier U, Deslandes L, Somssich I E, Ullah H ("*Arabidopsis* scaffold protein RACK1A interacts with diverse environmental stress and photosynthesis related proteins," *Plant Signal Behav.,* 2013; 8:e24012). Moreover, while wild-type RACK1A scaffold protein, when used as bait, could interact with almost 100 different proteins, RACK1A-Y248F bait failed to interact with any protein. Kundu N, Dozier U, Deslandes L, Somssich I E, Ullah H ("*Arabidopsis* scaffold protein RACK1A interacts with diverse environmental stress and photosynthesis related proteins," *Plant Signal Behav.,* 2013; 8:e24012), implicating the residue in the functional regulation of RACK1 protein. It is quite possible that post-translational modifications, like Y248 phosphorylation, are needed to stabilize the RACK1A protein. Sabila M, Kundu N, Smalls D, Ullah H. ("Tyrosine Phosphorylation Based Homo-dimerization of *Arabidopsis* RACK1A Proteins Regulates Oxidative Stress Signaling Pathways in Yeast," Front *Plant Sci.* 2016; 7:176); Link A J, Eng J, Schieltz D M, Carmack E, Mize G J, Morris D R, Garvik B M, Yates J R 3$^{rd}$ ("Direct analysis of protein complexes using mass spectrometry," *Nat. Biotechnol.,* 1999; 17:676-82); Ji H, Fraser C S, Yu Y, Leary J, Doudna J A ("Coordinated assembly of human translation initiation complexes by the hepatitis C virus internal ribosome entry site RNA," *Proc. Natl. Acad. Sci.* U.S.A, 2004; 101:16990-95); Guo J, Wang S, Valerius O, Hall H, Zeng Q, Li J F, Weston D J, Ellis B E, Chen J G ("Involvement of *Arabidopsis* RACK1 in protein translation and its regulation by abscisic acid," *Plant Physiol.,* 2011; 155:370-83); Coyle S M, Gilbert W V, Doudna J A ("Direct link between RACK1 function and localization at the ribosome in vivo," *Mol. Cell Biol.,* 2009; 29:1626-34). Considering that RACK1 proteins homo/hetero-dimerize, it is hypothesized that the dimerization status of RACK1 proteins, dependent on Y248 residue phosphorylation, may dictate the regulation of specific signaling pathways by fine tuning affinities for interacting proteins.

Sabila M, Kundu N, Smalls D, Ullah H ("Tyrosine Phosphorylation Based Homo-dimerization of *Arabidopsis* RACK1A Proteins Regulates Oxidative Stress Signaling Pathways in Yeast," *Front. Plant Sci.,* 2016; 7:176).

As viruses require host factors to translate their transcripts, targeting the host factor(s) offers a unique opportunity to develop novel antiviral drugs. In addition, the low variability of host factors targeted by host-targeted antivirals (HTAs) results in a high genetic barrier to resistance. Nathan C. ("Fresh approaches to anti-infective therapies," *Sci. Transl. Med.,* 2012, 4:140sr2). In this regard, we report here the identification of inhibitor compounds for the host protein RACK1, a protein that is utilized by many viruses for their own proliferation. The requirement for the Y248 residue phosphorylation for both homo-dimerization and interaction with diverse proteins has led us to target the site for isolating small compounds that could bind the Y248 pocket and thus prevent its phosphorylation. We hypothesized that functional inhibitor compounds of RACK1 may prevent the proliferation of those viruses that use host RACK1 protein for their mRNA translation.

Figure 2:
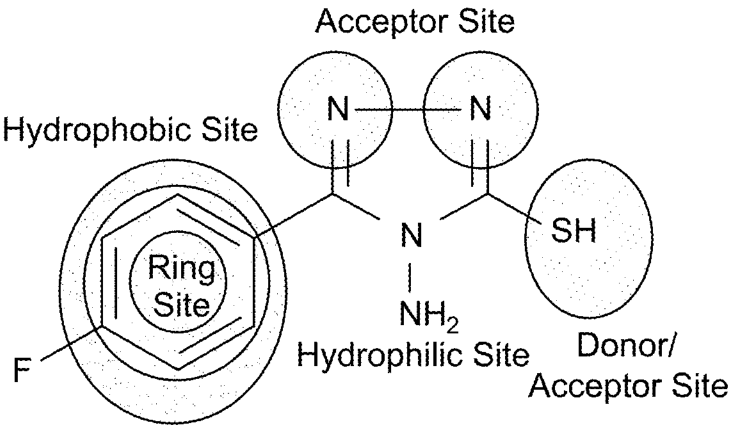
FIG. 2 shows ligand-based pharmacophore model generated on SD-29 with pharmacophore constraints acceptor, donor, hydrophobic ring, and hydrophilic sites represented by filled circles. Structures of compounds SD-29-12 and SD-29-14 are shown.
Figure 2:
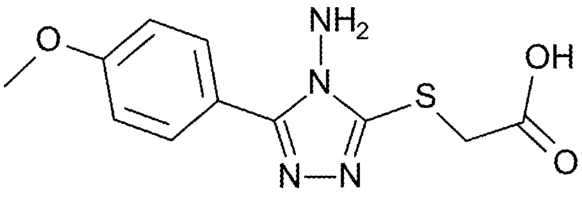
Figure 2:
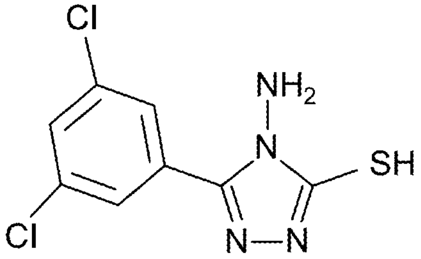

SD-29 is Identified as a Potent Binder to the RACK1A Y248 Phosphorylation Pocket By the implementation of a structure based drug design approach, the best-fitting candidate RACK1A Y248 pocket binding small compound—SD-29 the 4-amino-5-phenyl-1,2,4-triazole-3-thiol class of compounds has been identified and its analogs are used to provide precise regulation of reported RACK1 mediated specific viral proliferation. To isolate the best-fit compounds, the multi-step screening approach, in which each step acts as a filter comprised of protein conformation sampling to account for flexibility of unbound proteins prior to docking simulations, has been used. To generate the pharmacophore model, the relative positions of the donor/acceptor sites and hydrophobic centers were used as potential pharmacophore sites. The acceptor (A), donor (D), hydrophobic sites, and negative/positive centers were defined with various macro, spatial and constraints features with exclusion spheres centered on the receptor site. A pharmacophore match search was performed on a small molecule database that contains five million commercially available compounds, including natural product compounds. FIG. 1 shows a receptor-based pharmacophore model generated on the Y248 RACK1A site (phosphorylation site) with exclusion spheres. To get appropriate docking, the exclusion spheres were used up to 8A region from the binding site region. Using this strategy, a candidate compound, SD-29 that putatively binds to RACK1A Y248 (FIG. 3) has been identified. Using the identified SD-29 structure, a ligand pharmacophore model with various macros, spatial and constraints features defining centroid, acceptor (A), donor (D), and hydrophobic sites/centers was developed to aid in further identification of additional compounds (FIG. 2).

Figure 3:
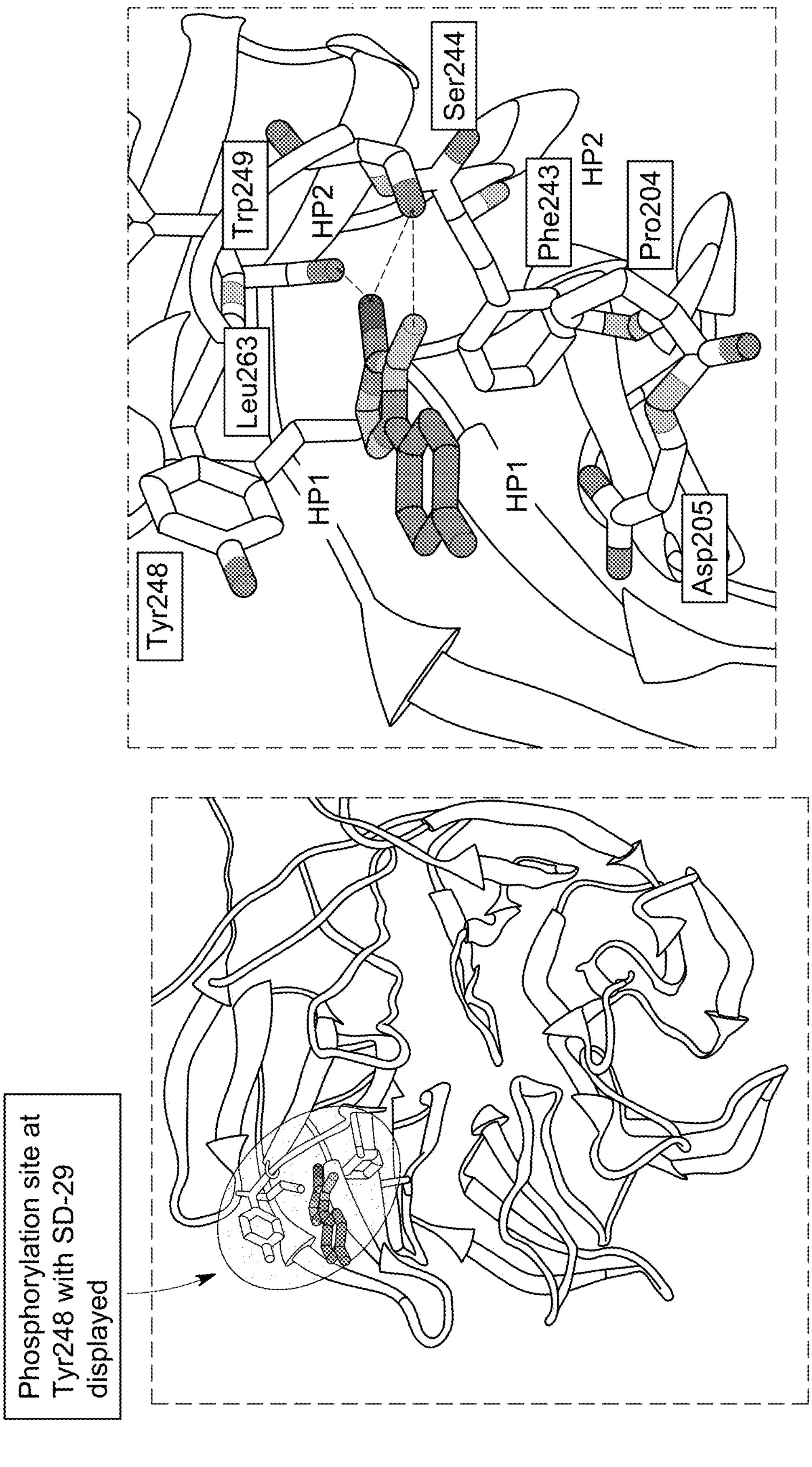
FIG. 3 shows a docked Model of RACK1A with SD-29 at the Y248 phosphorylation site. (left panel) Modeled structure of RACK1A with SD-29 (carbon in green) docked into it. The targeted binding pocket is highlighted in green. RACK1A is shown as a ribbon model (white). (right panel) Detailed view of the SD-29 (carbon in green) interaction with RACK1A site pocket. The residues interacting with SD-29 are shown in a ball-and-stick model. Hydrogen bonds are shown as red broken lines. The SD-29 binding site is surrounded by both hydrophobic (HP1) and hydrophilic residues (HP2). The structural model of 'SD-29' with RACK1A shows hydrogen bonds with Ser244, Trp249 and hydrophobic interactions with Tyr248, Phe243, Pro204, Leu263 and Trp249 residues.
Figure 6:
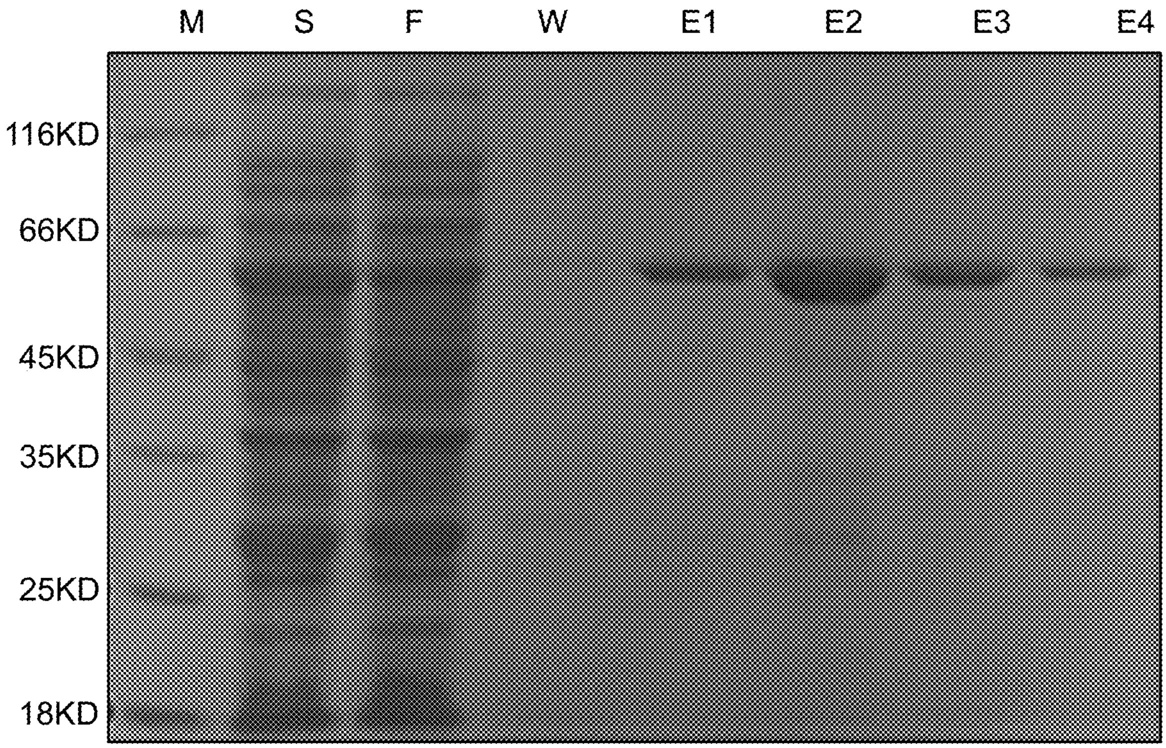
FIG. 6 shows purified RACK1 protein on a SDS-PAGE gel. An *E. coli* BL21(DE3) host strain was transformed with recombinant plasmid containing rice RACK1 (Chr05Os05g47890) cDNA with a 3' His tag. PMSF-induced bacterial lysate eluted from the glutathione-resin column was resolved by the SDS-PAGE electrophoresis for purity check. Lane M: Protein Marker; Lane S: Supernatant; Lane F: Flow through of supernatant; Lane W: Wash; and Lane E1~4: Elutions.
Figure 7:
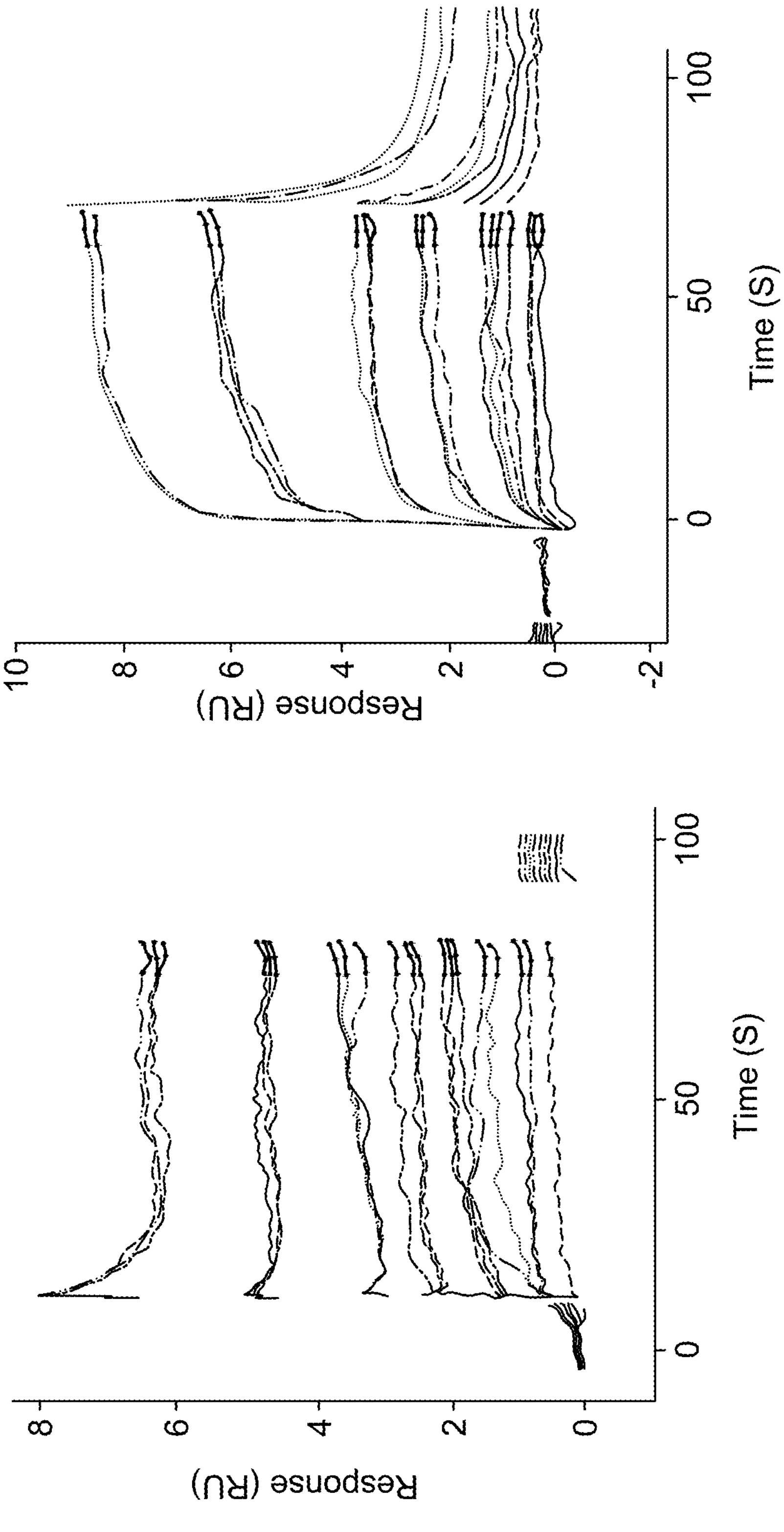
FIG. 7 shows a result demonstrating that in the SPR assay, SD-29 (left panel) and SD-29-12 (right panel) bind directly to immobilized RACK1A on the surface of the chip via similar patterns, as evident in the sensogram. SD-29 (left panel) and SD-29-12 (right panel) were separately injected three times on the CM5 chip at 0, 1.56 μM, 3.13 μM, 6.25 μM, 12.5 μM, 25 M, 50 μM, and 100 μM (top sensor) concentrations (left panel) and at 3.13 μM, 6.25 μM, 12.5 M, 25 μM, 50 μM, and 100 μM (top sensor) concentrations (right panel).

FIG. 3 shows the docked model of RACK1A with the most potent small compound (SD-29) at the Y248 phosphorylation pocket. The detailed view of SD-29 (carbon in green) interaction with the RACK1A binding site, indicates that SD-29 potentially form hydrogen bond with Ser244 and Trp249, and maintains hydrophobic interactions with Try248, Phe204, Leu263, and Trp249 residues. In order to obtain in vitro confirmation of the binding of the isolated compounds to the purified RACK1A protein, recombinant RACK1A protein from rice was raised in *E. coli* cells (FIG. 6). The small compound SD-29 and its structural analog (SD29-12) were used to evaluate their binding potential with the recombinant RACK1A proteins. The compounds were examined for their ability to interact directly with wild-type recombinant protein immobilized on the Surface Plasmon Resonance (SPR) chip. The SPR assays showed that the compounds SD-29 and SD29-12 bound strongly to recombinant RACK1A protein with an $KD_{50}$ value of 42 μM and 58 μM, respectively (FIG. 7). This in-vitro confirmation of binding of the compounds to RACK1A protein has led to us to investigate whether the binding has any effect on the reported host factor RACK1 mediated virus proliferation.

Compounds can Potentially Inhibit Stress-Induced RACK1A Y248 Phosphorylation

Figure 4:
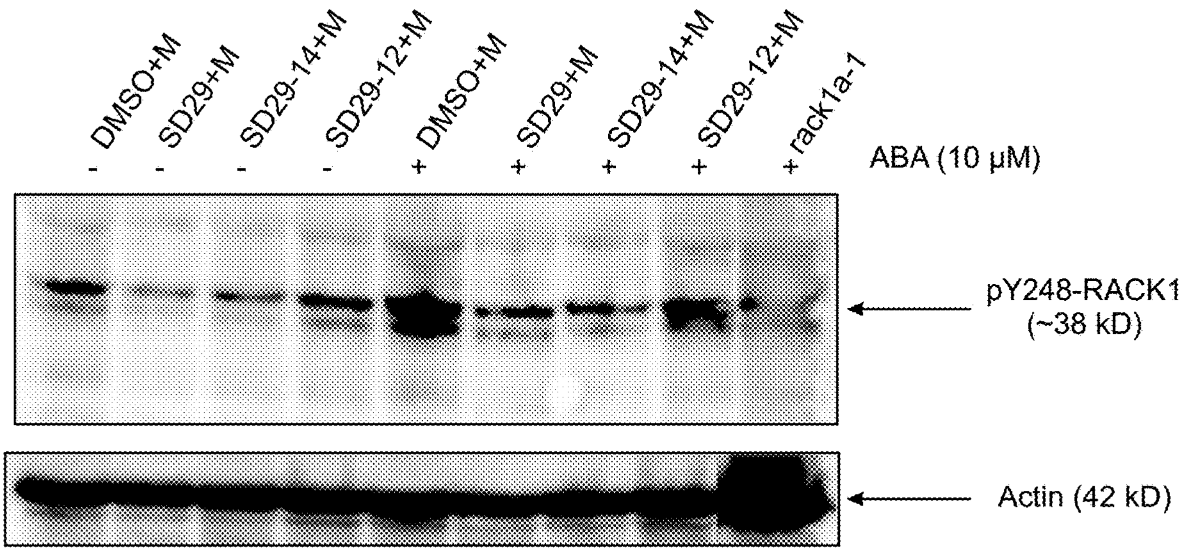
FIG. 4 shows a result demonstrating that RACK1 functional inhibitor compounds inhibit stress hormone induced RACK1A Y248 phosphorylation. One-week old *Arabidopsis* seedlings were treated with 10 μM of stress hormone Abscisic acid (ABA) in the presence/absence of the inhibitor compounds for 12 hours in a growth chamber (overnight) at 22° C. Lysates were probed with an antibody raised to detect phosphorylated Y248 residue of RACK1A protein in *Arabidopsis*. Lysates from rack1a-1 knock-out mutant seedlings grown and treated similarly as the wild-type seedlings were used as a negative control. The compounds were dissolved in DMSO (D) and ABA was dissolved in methanol (M). The lower panel shows the same membrane stripped with stripping buffer and then probed with an *Arabidopsis* Actin antibody to show the loading control.

In order to evaluate whether SD-29 can specifically inhibit RACK1A tyrosine phosphorylation, particularly on the Y248 residue, an anti-phospho-Y248-RACK1 antibody was raised commercially (Creative Diagnostics, NY). To ascertain whether the antibody only recognizes the *Arabidopsis* Y248 in the RACK1A protein, and not in the RACK1B or RACK1C proteins, the RACK1A-specific phospho-peptide (10 residues) was adsorbed against the non-phosphorylated RACK1A, RACK1B and RACK1C peptides and the adsorbed phospho-peptide was used as the antigen in rabbit. RACK1A Y248 phosphorylation has previously been identified as a key event needed for RACK1 mediated scaffolding activities by regulating protein-protein interactions in plants. Kundu N, Dozier U, Deslandes L, Somssich I E, Ullah H. ("*Arabidopsis* scaffold protein RACK1A interacts with diverse environmental stress and photosynthesis related proteins," *Plant Signal Behav.,* 2013; 8:e24012); Sabila M, Kundu N, Smalls D, Ullah H. ("Tyrosine Phosphorylation Based Homo-dimerization of *Arabidopsis* RACK1A Proteins Regulates Oxidative Stress Signaling Pathways in Yeast," *Front. Plant Sci.,* 2016; 7:176). The corresponding residue in human RACK1 is also a key requirement for scaffolding activities needed at the receptor level. Chang B Y, Chiang M, Cartwright C A ("The interaction of Src and RACK1 is enhanced by activation of protein kinase C and tyrosine phosphorylation of RACK1," *J. Biol Chem.,* 2001, 276:20346-56). As RACK1A is known to regulate the diverse stress responses in plants, Islas-Flores T, Rahman A, Ullah H, Villanueva M A ("The Receptor for Activated C Kinase in Plant Signaling: Tale of a Promiscuous Little Molecule," *Front. Plant Sci.* 2015; 6:1090), we investigated the role stress hormone abscisic acid on the RACK1A Y248 phosphorylation. It is known that ABA mediated signaling pathways regulate diverse biotic and abiotic stresses including salt and drought stresses (Fernando V C D, Schroeder D F. (Feb. 17, 2016) "Role of ABA in *Arabidopsis* Salt, Drought, and Desiccation Tolerance," Abiotic and Biotic Stress in Plants—Recent Advances and Future Perspectives, Shanker A K and Shanker C, IntechOpen), and RACK1A has been implicated in the ABA mediated stress pathways in *Arabidopsis*. Guo J, Wang J, Xi L, Huang W D, Liang J, Chen J G ("RACK1 is a negative regulator of ABA responses in *Arabidopsis," J. Exp. Bot.,* 2009, 60:3819-33). Therefore, we used young *Arabidopsis* seedlings treated with/without ABA for 12 hours to mimic stress conditions. As a control, we used lysates from the rack1a-1 knock-out seedlings. While the actin antibody shows the almost equal loading, the presence or absence of ABA showed a significant role on the RACK1A Y248 phosphorylation (FIG. 4). The lane with ABA but no inhibitor compounds clearly showed that the Y248 residue of RACK1A proteins were highly phosphorylated, while the inhibitor compounds (SD 29 and SD 29-14) prevented the ABA-induced Y248 phosphorylation which showed almost as the same level without the stress hormone present (FIG. 4). Note that, the antibody was raised by using RACK1A Y248 phosphorylated peptide as immunogen and by adsorbing against the non-phosphorylated RACK1A, RACK1B, and RACK1C peptides. Comparing with the negative control and considering the scheme to raise the antibody, it can be concluded that the SD29, SD29-14, and SD29-12 to a lesser extent, can potentially inhibit the stress induced Y248 phosphorylation.

Figure 5:
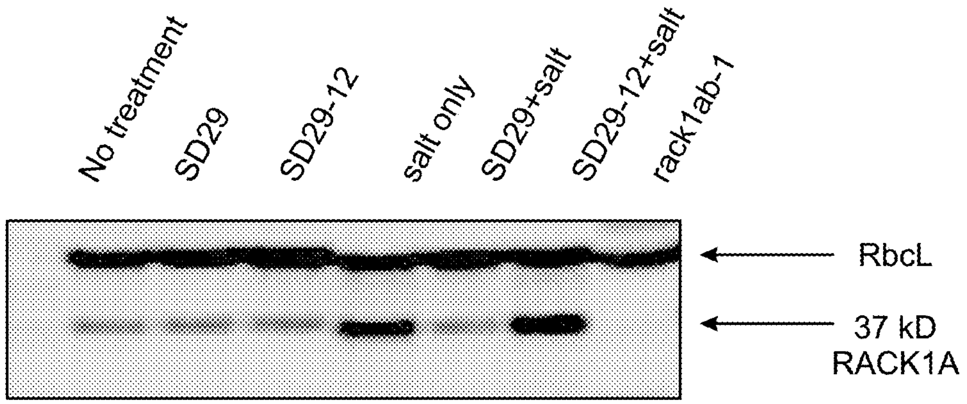
FIG. 5 shows a result demonstrating that salt stress-induced upregulation of RACK1 expression was inhibited by SD-29. The abundant leaf protein Rubisco large subunit (RbcL) was used as a loading control for the blot. The 37 kD RACK1 band was absent from the genetic knockout of RACK1 plants (double mutant-rack1ab lane).

The reported positive expression of RACK1A protein under salt stress condition in *Arabidopsis* has led us to examine the RACK1A expression in the presence and absence of the inhibitor compounds during salt stresses. We determined that the RACK1A protein expression was specifically modulated by the inhibitor compounds when the lysates with salt or without salt in the presence and absence of the small compounds were probed with an antibody raised by using the full length RACK1A protein as antigen. (Agrisera, Vännäs, Sweden, FIG. 5). When challenged with salt stress, SD-29, but not its analog SD29-12, inhibited RACK1 protein expression. However, whether the effect of SD29-12 is *Arabidopsis* salt stress specific condition needs further experimental evidence. As the antibody cross-reacts with all three RACK1 isoforms in *Arabidopsis*, we used the double knockout (rack1ab) as a negative control on the blot (triple mutant is lethal at the early seedling stage). The large subunit of the abundant leaf protein rubisco (RbcL) was used as loading control for this blot. As the results support the in-silico based prediction, we set out to investigate the effect of the compounds on the mammalian RACK1 based virus proliferation.

HSV-1 Infection Induced RACK1 Expression

Since RACK1 is an important factor for protein translation, we wondered whether RACK1 expression is regulated by viral infection. We tested this hypothesis in a HSV-1 infection system in the HEp-2 cell line. This cell line was selected because the human RACK1 target site Y246 shows strong similarity to the *Arabidopsis* Y248 pocket. First, we infected HEp-2 cells with HSV-1 at an MOI of 1.25. The whole cell lysates were collected at different time points as indicated in panel A of FIG. 8. The samples were run on an SDS PAGE gel and the proteins were transferred to a membrane which was blotted with antibodies for viral proteins (ICP0, ICP8, and gD) and for cellular proteins (RACK1 and tubulin). RACK1 was induced at the very beginning of the viral infection (2 hpi), as can be seen by comparing the levels of RACK1 after viral infection to that of 0 hpi (panel A of FIG. 8). The increasing protein level of RACK1 reached its peak at 8 hpi. We then wondered whether RACK1 upregulation is related to the viral concentration. For that purpose, we infected HEp-2 cells with different MOIs of HSV-1 for 24 hours to examine the levels of RACK1. RACK1 levels were increased after viral infection and the increase in RACK1 was proportionally associated with the MOI of virus (panel A of FIG. 8). Therefore, HSV-1 infection induces the production of RACK1 at very early time points after infection and the level of RACK1 upregulation is dependent on viral dose. In addition, as expected all the viral proteins were up-regulated with increasing viral loads and at increasing time-points (panel A of FIG. 8). The results helped establishing the concentration and time-points needed to see whether the compounds have any effect on the viral proliferation that is marked by the increasing synthesis of viral proteins.

SD-29 has Repressive Effects on Viral Protein Production

Figure 8A:
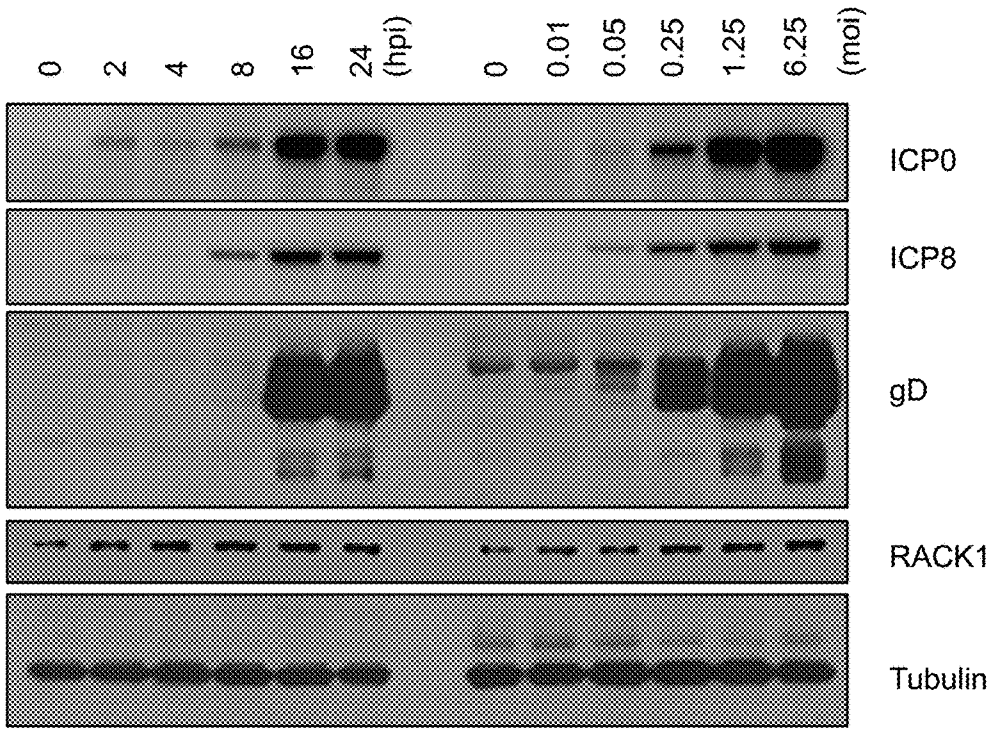
FIG. 8 shows effects of the compounds on HSV-1 protein expression. Panel A of FIG. 8 depicts time and concentration dependent virus protein expression to deduce an optimum drug treatment regimen. Left panel shows the time dependent HSV-1 virus protein expression after infection with HSV-1 17 at an MOI 1.25. Right panel shows the same virus protein expression under different concentrations of virus starting from 0.01 to 6.25 MOI. Panel B of FIG. 8 shows a result demonstrating that Hep-2 cells were pre-treated with the compounds for 24 h, and three different virus proteins (ICP0, ICP8, and gD) were assayed 24 h post infection with different titers of HSV-1. Red arrows show the downregulated virus proteins, and the blue arrow shows the down-regulated RACK1 protein. Tubulin expression was used as the loading control for the blots.
Figure 8B:
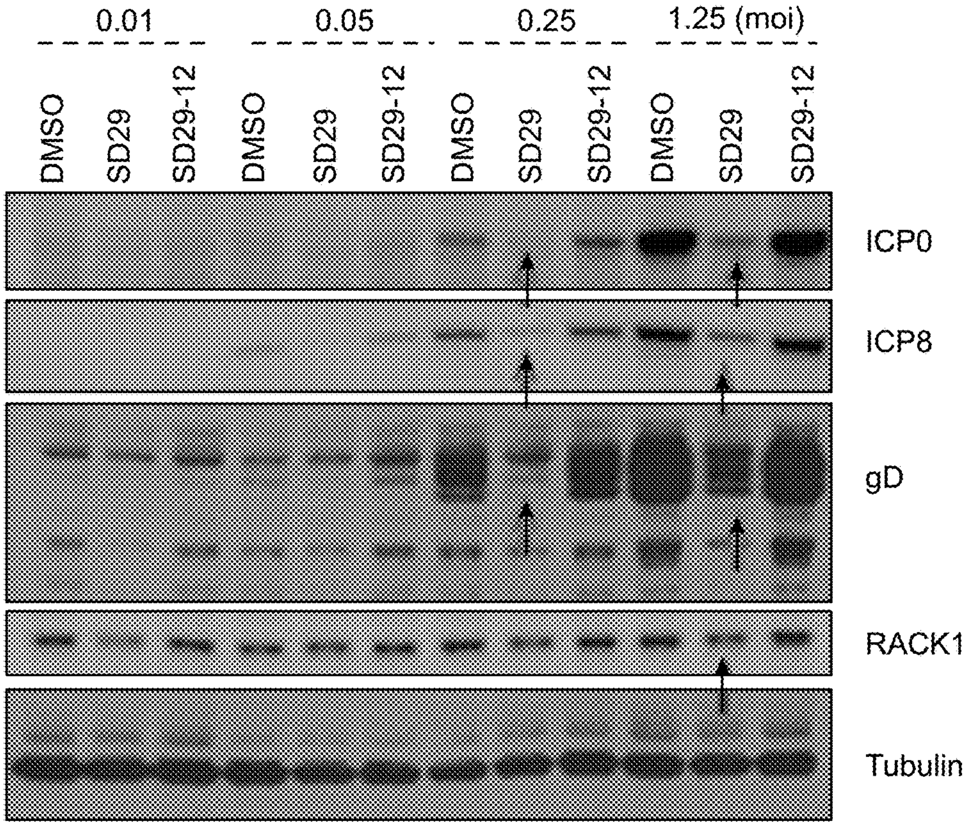

To determine whether the small compound SD-29 that binds to RACK1A protein and inhibits Y248 phosphorylation, has any effects on viral protein production, we treated HEp-2 cells with SD-29, its analogue (SD29-12), or DMSO for 24 hours at 100 μM, and then the cells were infected with different MOIs of HSV-1 (panel B of FIG. 8). Twenty-four hours after infection, the whole cell lysate samples were subjected to western blot assay to examine the viral and cellular proteins. SD-29 reduced the production of RACK1 as compared to the DMSO or SD-29-12 control treatment groups (panel B of FIG. 8). Clearly, viral protein levels from SD-29-treated HEp-2 cells were lower than that of DMSO- or SD-29-12-treated HEp-2 cells. We examined three HSV-1 proteins: ICP0 is an immediate early (IE) protein, ICP8 is an early (E) protein, and gD is a late (L) protein. Therefore, our results demonstrated that SD-29 repressed HSV-1 protein production, which can effectively inhibit virus proliferation in the cell line.

Compound's Effect on HSV-1 Gene Transcription

Figure 9:
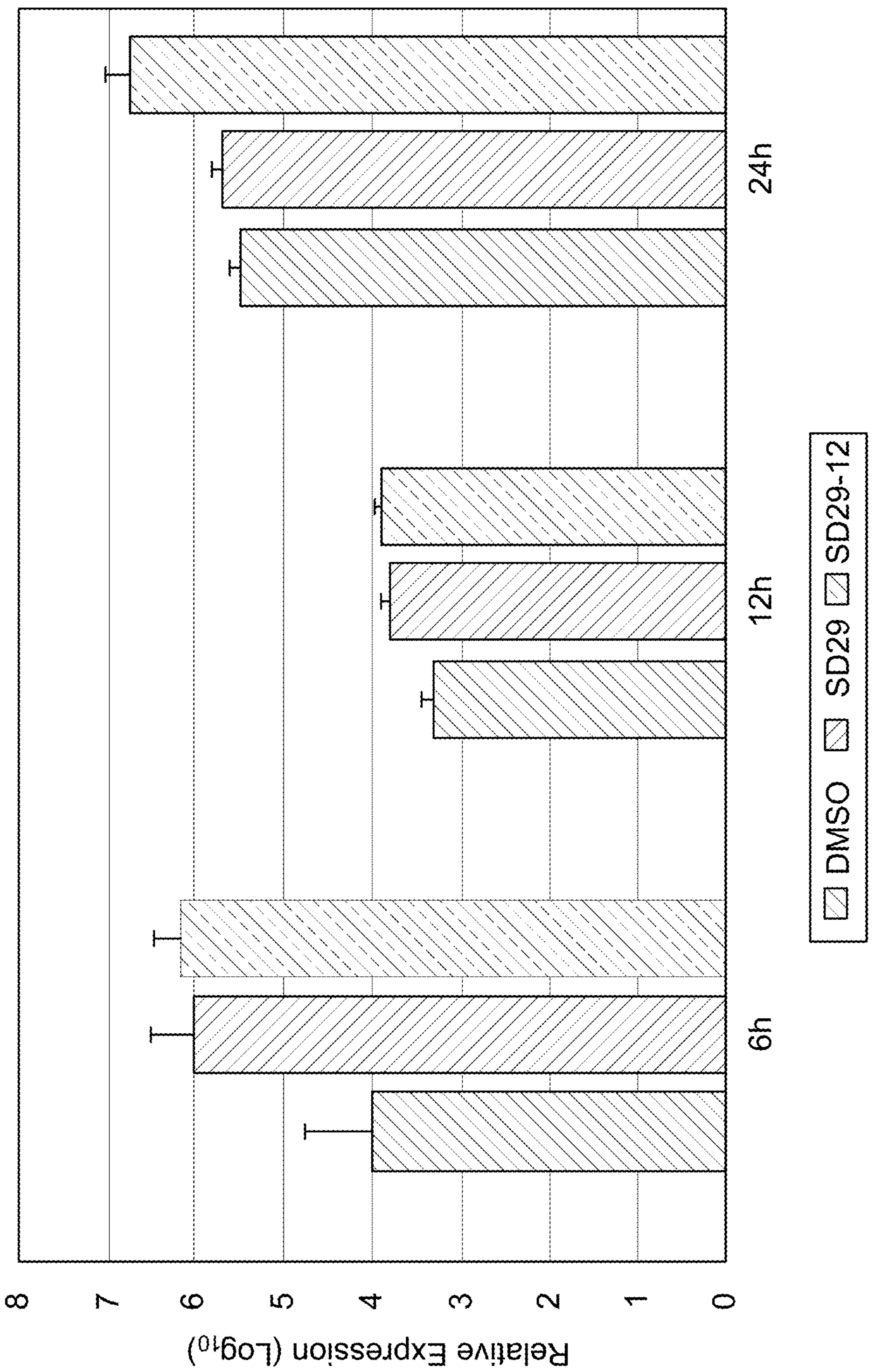
FIG. 9 shows a real-time PCR analysis of HSV-1 ICP0 expression in Hep-2 cells treated with the indicated inhibitor compounds and DMSO (as control) for the indicated time points. The total transcript levels were quantified using actin expression as an internal control. The cDNA obtained immediately after the virus and drug transfection(s) was set as a baseline value. The normalized expression values were transformed to the $\log_{10}$ value. The data plot represents mean±standard error calculated from three replicates.

Since RACK1 is an important chaperone protein for ribosome function in mRNA translation, we assumed that SD-29 might affect viral gene expression only at the translational level. The compounds were developed to specifically inhibit the RACK1 protein; therefore, it is not expected to affect the mRNA production of assayed proteins (FIG. 8). To investigate whether SD-29 is functioning as expected, the mRNA expression level of the ICP0 gene was measured in qPCR assay (FIG. 9). Though initially after the infection, the HSV-1 ICP0 transcript level was upregulated to some extent by the compounds, over time the effect subsided and fall at the same level as with the DMSO treated samples (FIG. 9). Note that the assayed gene ICP0 is an immediate early gene and the ICP0 protein is capable of transactivating promoters from all three kinetic classes of HSV-1 genes, including immediate-early, early and late. Therefore, high level of transcripts at the early stage of infection may reflect an adaptive response to the challenge by the compounds. The compound treated (SD-29, SD29-12) and non-treated (DMSO) samples essentially showed the same level of ICP0 mRNA at 12 and 24 hpi after showing slight upregulation initially (FIG. 9). The results establish the specificity of the SD-29 in inhibiting the level of key proteins needed by the HSV-1 to proliferate while not affecting mRNA levels.

SD-29 Inhibits Viral Proliferation

To assess the efficacy of SD-29 on the HSV-1 proliferation, a plaque assay was performed. We wanted to quantitatively assess whether SD-29 could inhibit viral replication. Because HSV-1 was able to enter cultured HEp-2 cells, we evaluated whether this entry led to productive virus replication. The cytopathic effect in the form of plaque formation increased significantly over time in virus-infected HEp-2 cells treated with vehicle, as seen in Table 1. As shown in Table 1, inoculum harvested from infected HEp-2 cells treated with DMSO produced a larger number of plaques 24 hours post infection. In contrast, cells infected with identical doses of the same virus and treated with SD-29 failed to produce significant infectious virions. These results, together with those of the entry assay, show that treatment with SD-29 led to the inhibition of a productive infection.

TABLE 1

| Plaque formation unit (pfu) assay | | | |
|---|---|---|---|
| | DMSO | SD-29 | SD29-12 |
| 0 hpl | 0 ± 0 | 0 ± 0 | 0 ± 0 |
| 6 hpl | 3.2 ± 0.08 × $10^2$ PFU/mL | 0 ± 0 | 3.8 ± 0.07 × $10^2$ PFU/mL |
| 12 hpl | 2.6 ± 0.03 × $10^3$ PFU/mL | 1 ± 0.08 × $10^2$ PFU/mL | 3.6 ± 0.04 × $10^3$ PFU/mL |
| 24 hpl | 1.9 ± 0.02 × $10^6$ PFU/mL | 1.8 ± 0.04 × $10^5$ PFU/mL | 2.6 ± 0.03 × $10^6$ PFU/mL |

In Table 1, confluent monolayers of HEp-2 cells were infected with serially diluted HSV-1 virus and were fixed and Giemsa stained at 0, 6, 12, and 24 hr post infection. The numbers of plaques were visualized. The number of plaques formed post infection decreased in the presence of SD-29 in a time-dependent manner.

In order to assess whether the compounds are producing any toxicity that can led to the cell deaths, we evaluated the cell viability by the trypan blue exclusion method. As long-term inhibition of RACK1 expression has been reported to cell cycle arrest, we limited our experimental treatments to 24 h and evaluated the cell viability of almost full confluent cells after 24 h of compound treatment. As can be seen in Table 2, the compounds at 24 h post-treatment did not cause any major cell viability problem (because with or without the compounds, the cells maintained over 90% viability).

TABLE 2

HEp-2 Cell viability after 24-hour treatment with 10 or 100 μM concentration of the inhibitor compounds

| Compounds | Mean | Std error (±) |
|---|---|---|
| DMSO (Control) | 96.0 | 4.18 |
| SD-29 (100 μM) | 92.7 | 2.38 |
| SD-29 (10 μM) | 94.0 | 5.79 |
| SD-29-14 (100 μM) | 93.7 | 2.17 |
| SD-29-14 (10 μM) | 97.5 | 2.06 |
| SD-29-12 (100 μM) | 97.7 | 0.43 |
| SD-29-12 (10 μM) | 92.7 | 3.96 |

In table 2, the viability of cells was measured with Trypan blue exclusion assay in a Cellometer (Nexcelom, Lawrence, MA). The percentage survival of the compound treated cells was evaluated along with the DMSO treated cells. The values represent the mean f SE of three separate well based replicates.

Visualization of the Compound Induced Inhibition of HSV-1 Proliferation

Figure 10A:
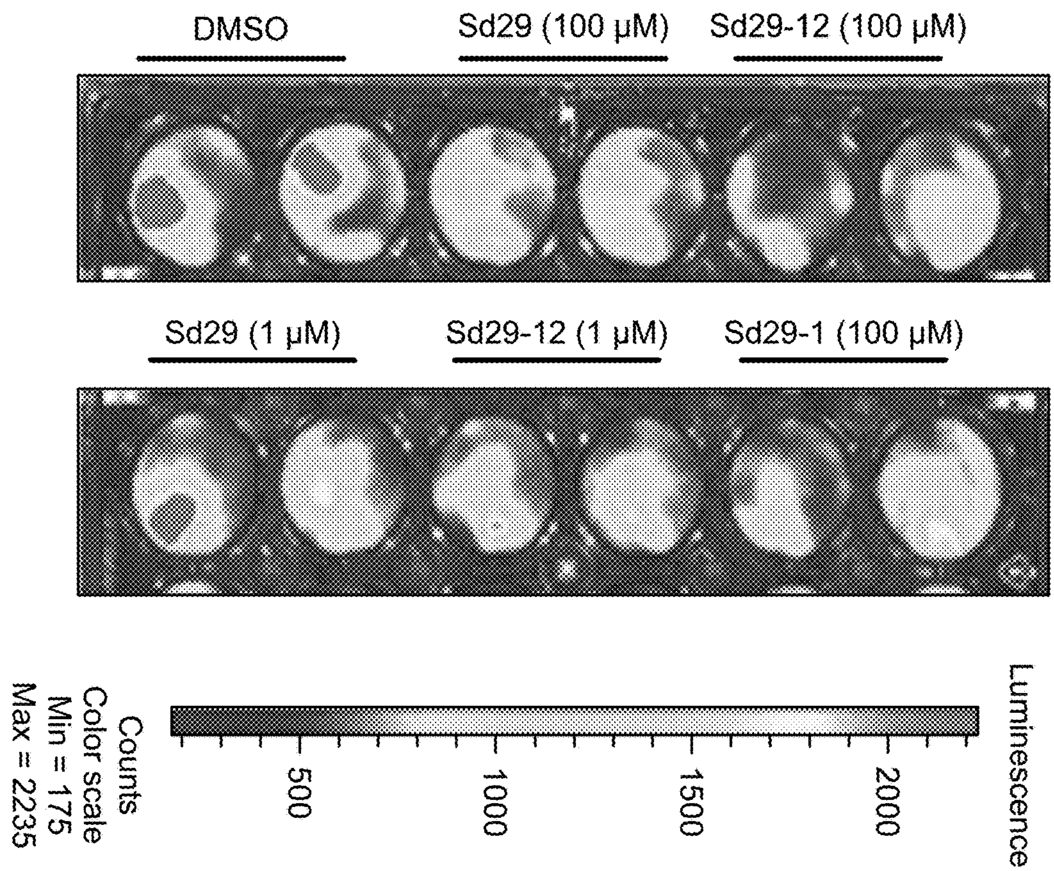
FIG. 10 shows that co-treatment of drugs with virus increases efficacy. Panel A of FIG. 10 shows the effect of drugs at the indicated concentrations after 24-hour post-infection with HSV1-Luc ($4\times10^6$ pfu/ml media), and the same treatments are shown in duplicates. Panel B of FIG. 10 depicts a result of assaying HSV-1 major structural protein ICP0 expression from the 48-hour post infection samples as shown in FIG. 10, panel A. The expression of tubulin was used as loading control (lower panel).
Figure 10B:
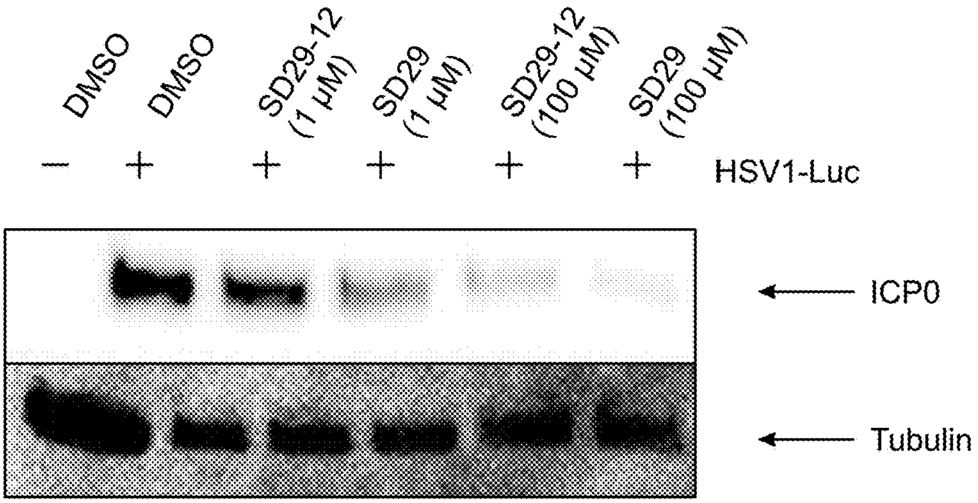

To visualize the effect of the drugs on the proliferation of HSV-1, a luciferase tagged HSV-1 F strain expressing luciferase (R8411 mutant) under the control of ICP27 promoter was obtained. Horsburgh B C, Hubinette M M, Tufaro F ("Genetic manipulation of herpes simplex virus using bacterial artificial chromosomes," *Methods Enzymol.,* 1999, 306:337-52). The co-treatment of the drugs and the virus at the same resulted in a dose dependent lowering of luciferase signals, indicating an inhibitory effect of the compounds (panel A of FIG. 10). The same samples after incubation of 48 h were used to assay for HSV-1 ICP0 and RACK1 protein expression (panel B of FIG. 10). Depletion of RACK1 by the compounds correlated with the depletion of the viral ICP0 protein confirming earlier results shown in panel B of FIG. 8.

An Analog of SD-29 Reveals Better Efficacy in the Inhibition of HSV-1 Proliferation Through similar docking experiments, an analog with chloro at the meta positions of the phenyl ring (SD29-14) instead of the mono-substituted (fluoro) at the para-position of the phenyl ring (SD-29) was isolated. SD29-14 analog showed strong inhibition of HSV-1 proliferation in a dose dependent manner (A of FIG. 6). While SD-29 showed much less efficacy at the 1 μM concentration, SD29-14 significantly inhibited the HSV-1 proliferation as evident by the lower luciferase signals. The luciferase signals were measured quantitatively and showed dose dependent inhibitory effect of the SD29-14 on the HSV-1 proliferation (panel B of FIG. 11). Availability of the compounds with better efficacy will allow application of the compounds at lower concentration which will circumvent any toxicity that higher concentration of compounds may pose. In addition, the better efficacy will allow the compounds to be tested against other IRES utilizing human pathogenic viruses as well.

SD29-14 Inhibits ICP0 Expression

Figure 12:
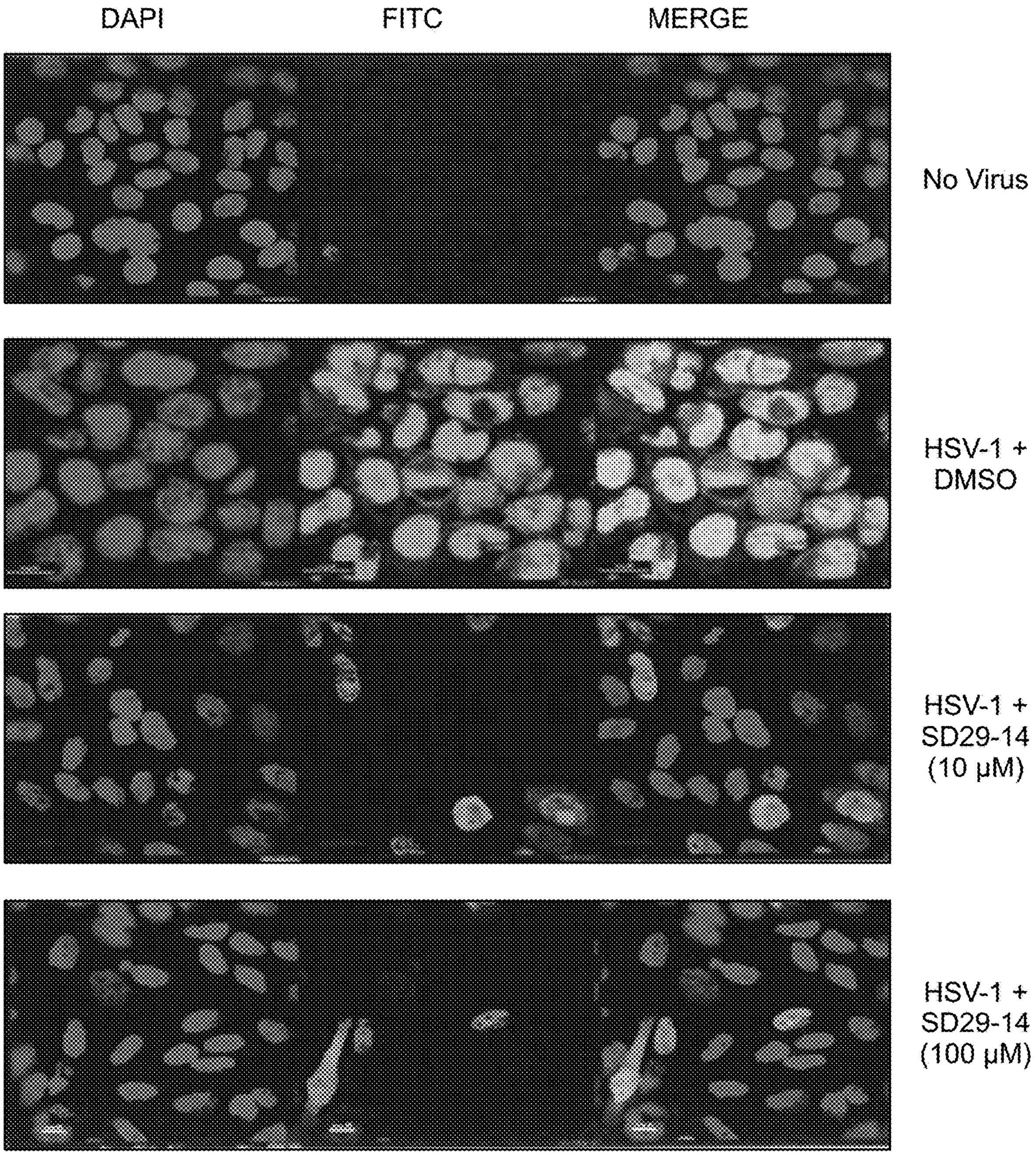
FIG. 12 shows visualization of HSV-1 proliferation inhibition by the RACK1 inhibitor compound SD29-14. The HEp-2 cells were infected with HSV-1 at an MOI of 1.0 for 30 h along with the indicated compounds and control. The cells were fixed with 4% paraformaldehyde and stained with anti-ICPO-FITC in green and DAPI (blue for DNA label in the nucleus). The slides were observed under a Nikon confocal microscope (60× magnification lens) and pictures were taken to show infected cells (green) and total cells (DAPI). All scale bars correspond to 20 μm. The imaging experiments were performed three independent times, and the results as shown are representative of one of three experiments.
Figure 13:
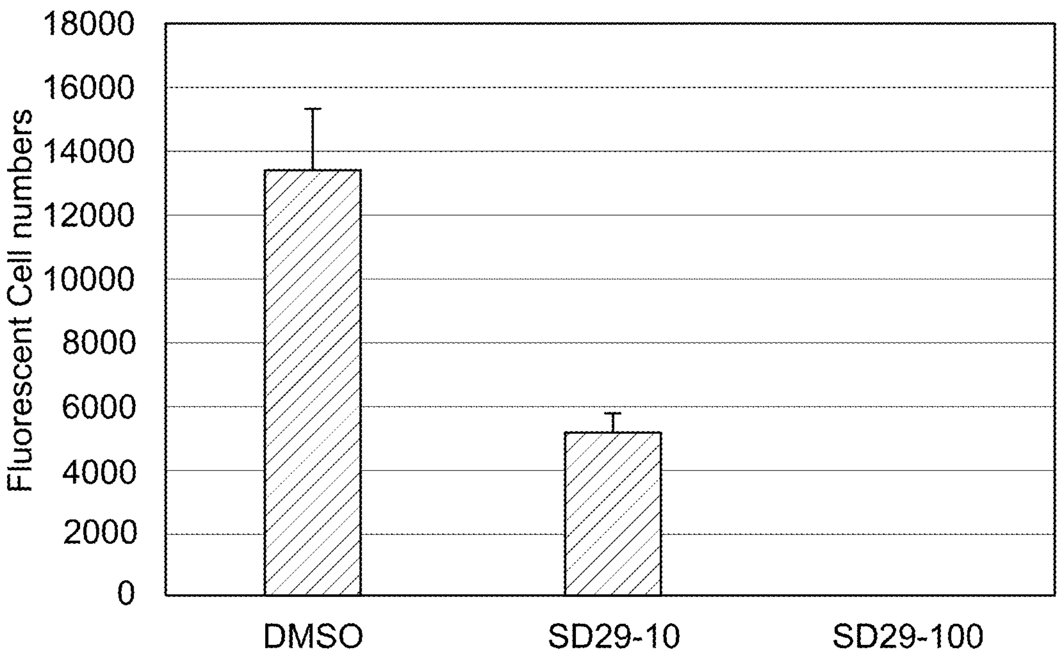
FIG. 13 depicts the quantification of fluorescent cells by Image based cell sorting in a Cellometer (Nexcelom Vision), based on the experiments depicted in FIG. 12. The Y-axis shows the total fluorescent cells per ml. The cells were prepared by immunostaining with ICP0 antibody after 24-h incubation with the indicated compounds. The total cell counts were $1.01\times10^6$/ml, $4.69\times10^6$/ml, and $5.36\times10^6$/ml for DMSO, SD29-14 (10 μM), and SD29-14 (100 μM) respectively. The numbers show the mean f SE of three replicates.

Our results provide evidence for the efficacy of the SD 29-14 against the HSV-1 proliferation, however, to further confirm this we set out to demonstrate via direct visualization the effect of the drugs on the proliferation of HSV-1 in living cells. In this regard, immunofluorescence studies were undertaken where HSV-1 ICP0 protein expression levels were visualized with or without the compounds with higher efficacy (SD29-14) in the Hep-2 cell line. We found that without treatment of the compound, the HSV-1 transfected cells express the viral ICP0 protein uniformly in the nucleus as it overlaps with the nuclear stain DAPI (FIG. 12), while treatment with 10 μM concentration of the compound effectively eliminated any expression of ICP0 protein from the cell (FIG. 12). The immuno-stained cells without any virus infection were used as a negative control (FIG. 12). Note that the absence of FITC stain is not due to the toxicity induced cell death. The DAPI staining of the same cells indicates that viable cells were present, but due to the presence of the compound a significant inhibition of viral proliferation was observed. The results as visualized by the FITC tagged secondary antibody indicate that HSV-1 proliferation is inhibited by the higher efficacy compound SD29-14 with a lower effective concentration.

Comparison of SD29-14 Efficacy with Known Anti-Herpes Drug Acyclovir

Figure 14A:
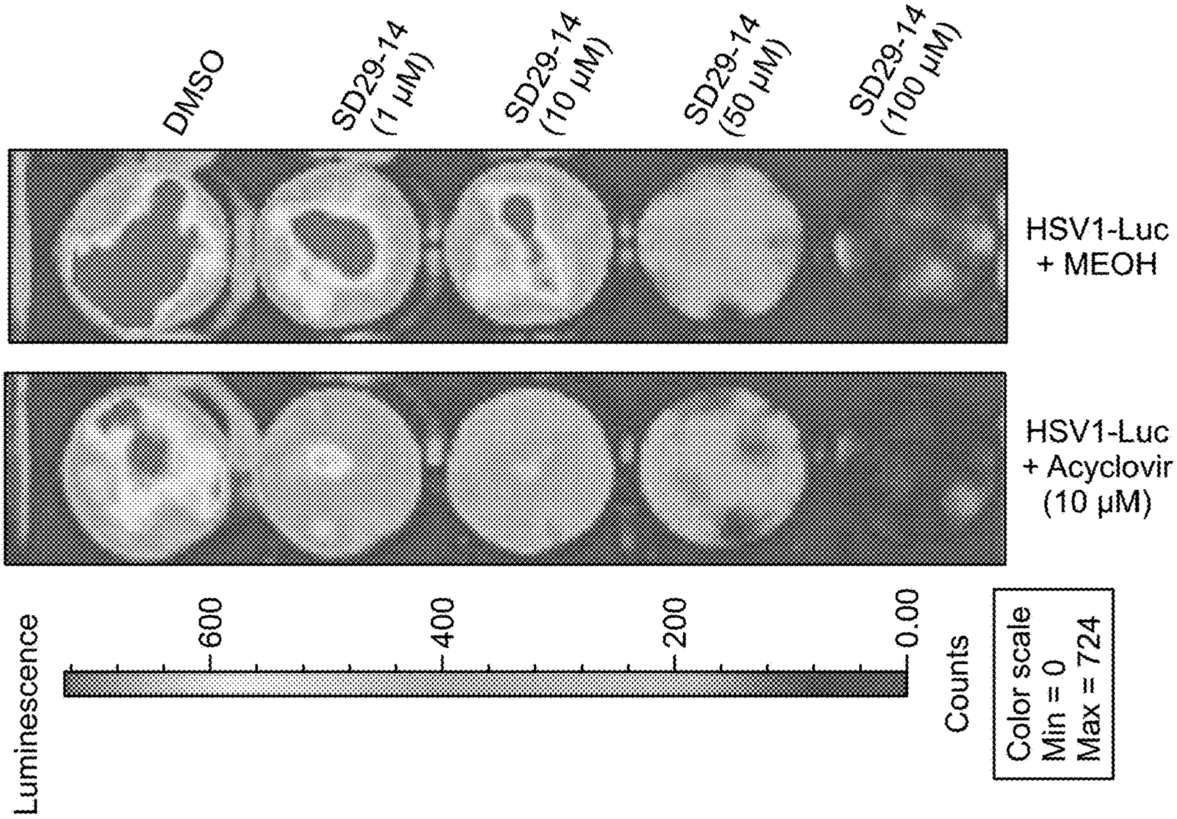
FIG. 14 shows efficacy of SD29-14 compared with the anti-herpes drug acyclovir. Hep-2 cells were incubated with the indicated compounds in the presence of HSV1-Luc virus at a concentration of $4\times10^6$ pfu/ml media (Panel A). Panel B depicts quantification of the luciferase signal from the samples in panel A. Signals from three replicates from two separate experiments were combined to generate the average and the standard error bar.
Figure 14B:
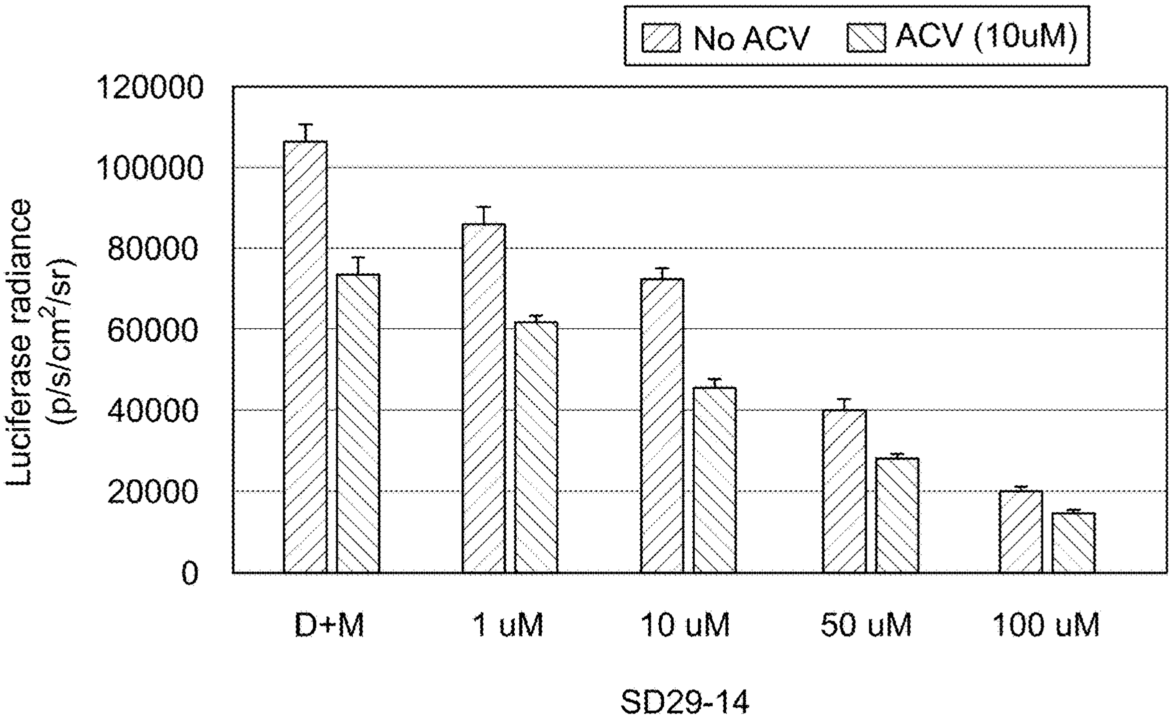
Figure 15:
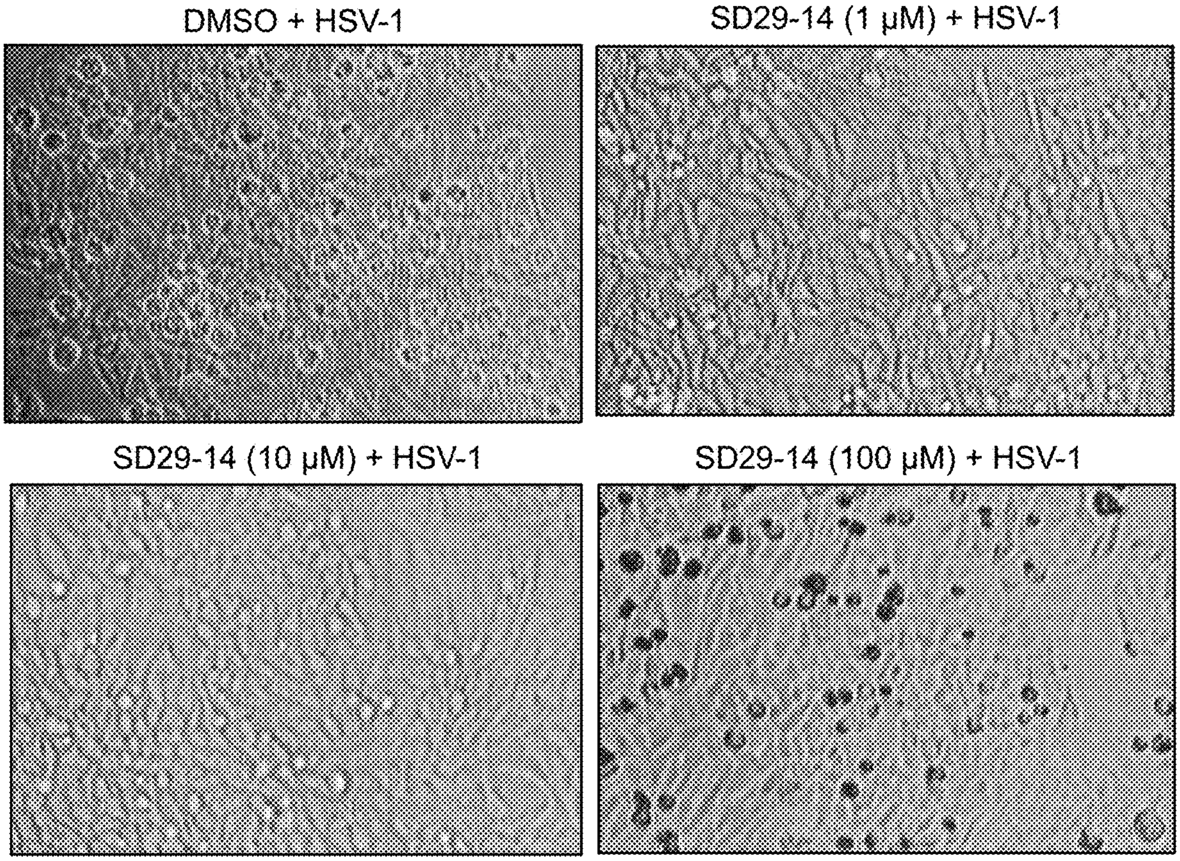
FIG. 15 depicts the results of in vitro testing to confirm the protective effect of a representative compound (SD-29-14) from the cytopathic effect caused by HSV-1. HEp-2 cells were grown to 80-90% confluency in Dulbecco's Modified Eagle's medium (DMEM) supplemented with 10% fetal calf serum (PCS) and 1% penicillin-streptomycin (PS) and 1% fungicide. The HSV-1 virus and the indicated concentration of compounds were added and incubated for 24 h. After washing away the virus with PBS, images were taken under a compound microscope. The DMSO treated cells show the highest amount of cytopathic effect (round structures); while the SD29-14 at different concentrations do not show the cytopathic effect. Note that at higher concentrations of SD29-14, few cells show darker cytopathic effect but the number of those cells are significantly less than that observed with the DMSO treated cells. Cells treated with the indicated compound were protected from the cytopathic effect of HSV-1 that was observed with the DMSO treatment (control).

Acyclovir is the major anti-herpes drug on the market and evaluated the SD29-14 efficacy with that of acyclovir. As can be seen from FIG. 14, application of SD29-14 could effectively inhibit the HSV1-Luc proliferation starting from 1 μM concentration (panel A of FIG. 14). As a very low concentration of acyclovir could not show the significant inhibition of HSV1-Luc (data not shown), we used the concentration of 10 μM at which point the drug showed inhibition of the HSV1-Luc proliferation. Our developed drug appears to show efficacy at slightly higher level than that of acyclovir induced effect. Acyclovir is known to be an inhibitor of viral DNA replication while SD29-14 is not known to regulate the viral DNA replication; therefore, we expected that there will be no interaction between the inhibitory pathways of these two drugs. In the absence of interaction, it is expected that the combinatorial treatment may potentially show synergistic effect in inhibition. Therefore, we treated the virus infected cells with different combination of the drugs. As can be seen from panel A of FIG. 14, a supralinear effect is apparent at all different concentrations of SD29-14 combined with 10 μM of acyclovir. When the luciferase signal is quantified, it shows a dose-dependent inhibition of HSV1-Luc proliferation in all concentrations of the drugs used either in combination or SD29-14 alone (panel B of FIG. 14). Acyclovir is known to be an inhibitor of viral DNA replication while our data show that SD 29-14 would not be known as or expected to be an inhibitor that can regulate viral DNA replication; therefore, there would have been an expectation that there would be no interaction between the inhibitory pathways of these two drugs, with their administration in combinatorial treatment therefore being additive (e.g., linear).

The data obtained from in vitro tests are consistent with a combinatorial treatment against a virus from the Herpesviridae family of viruses (e.g., a herpesvirus) comprising application of our compounds and an anti-herpes drug (such as a DNA polymerase inhibitor, e.g., a nucleoside analog antiviral agent, of which a synthetic analog of a purine nucleoside known as acyclovir is an example) as allowing an effective approach to combat HSV1 which is increasingly becoming resistant to the drugs available on the market.

Compounds were tested in which the compounds were according to Formula (4)

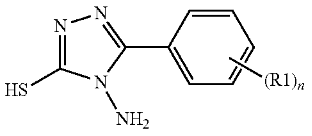

wherein n is an integer of 1 or 2, and each R1 is, independently, a halogen atom (e.g., bromo, chloro, fluoro or iodo). For instance, when n is 2, each R1 can represent the same halogen atom, or one R1 can represent one halogen atom and the other R1 can represent a different halogen atom. Representative compounds include the compounds designated SD 29-13 (phenyl moiety with 2,5-di-halogen substitution: 2-fluoro and 5-fluoro substitution), SD 29-15 (phenyl moiety with 2,4-mixed-halogen substitution: 2-fluoro and 4-chloro substitution), and SD 29-16 (phenyl moiety with 2,5 mixed halogen substitution: 2-fluoro and 5-bromo substitution).

The representative compounds were tested for efficacy when singularly administered and were also evaluated in an in vitro combinatorial treatment against a herpesvirus (Herpes Simplex Virus, HSV-1) in the same way reported above for SD 29-14, in a combinatorial treatment with another anti-herpes drug (acyclovir). A pro-drug can also be used.

SD 29-13

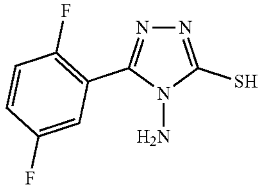

SD 29-15

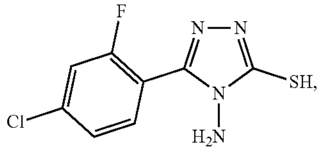

or

SD 29-15

SD 29-16

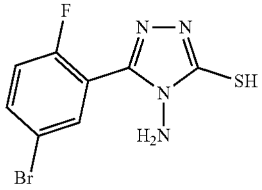

Compounds according to Formula (4) when n is 1 were evaluated. Compounds having para-halogen substitution, one designated SD 29 (phenyl moiety with para-fluoro substitution), and another designated SD 29-111 (phenyl moiety with para-chloro substitution), were tested for efficacy when singularly administered in vitro; and were also evaluated in an in vitro combinatorial treatment against a herpesvirus (Herpes Simplex Virus, HSV-1) in the same way reported above in a combinatorial treatment with an illustrative another anti-herpes drug (acyclovir). A pro-drug can also be used.

SD 29

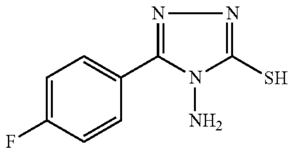

SD 29-111

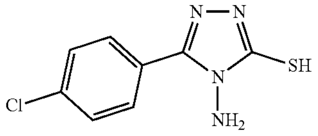

A compound according to Formula (5)

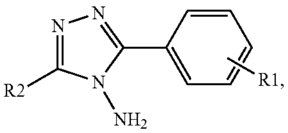

wherein R1 represents $C_1$-$C_6$ alkoxy substituted phenyl and R2 represents $—S—(CH_2)_m—COOH$ wherein m is 1, 2, or 3, was evaluated. An ester form of the compound can be used, e.g., a pharmaceutically acceptable salt or ester (e.g., methyl or ethyl ester) can be used. $C_1$-$C_6$ alkoxy includes straight chain alkoxy, such as methoxy, ethoxy, propoxy, butoxy, pentoxy; branched alkoxy, such as isopropoxy and iso-butoxy; and in principle $C_5$ or $C_6$ cyclic alkoxy. A $—CH(CH_3)—$ can be used instead of $—(CH_2)_m—$. The compound evaluated (SD 29-12) had as R1 a phenyl moiety mono-substituted at the para-position with methoxy; and m was 1. The compound was singularly administered in vitro, and also in vitro in a combinatorial treatment against a herpesvirus (Herpes Simplex Virus, HSV-1), by additionally administering another anti-herpes drug (e.g., acyclovir). The combinatorial treatment was carried out in the same way as reported above. A pro-drug can also be used.

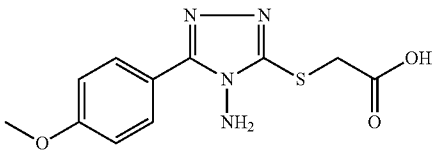 [SMILES: COc1ccc(-c2nnc(SCC(=O)O)n2N)cc1]

Figure 16:
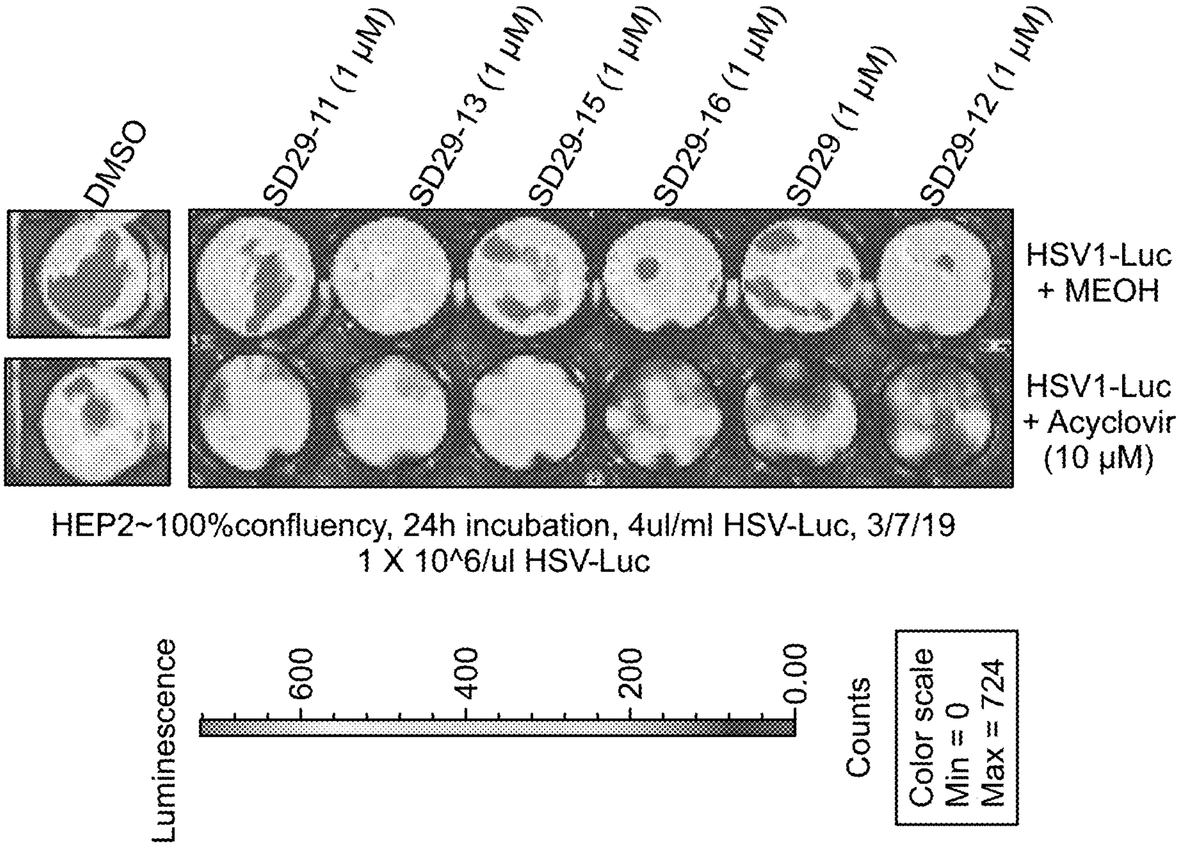
FIG. 16 shows a control (DMSO) on the far left and from there, going left to right, shows the identified compounds listed singularly (top) and in a combinatorial treatment (bottom) with a known anti-herpes drug (acyclovir).

FIG. 16 depicts the results of these experiments. Panels A and B show the control (DMSO) on the far left, and then going left to right, show the identified compounds listed singularly (top), and also in combinatorial treatment (bottom) with a known anti-herpes drug (acyclovir).

Example 2: RACK1 Inhibition Increases Annexin A2 Abundance

The present inventors envision that compounds of the present disclosure may be effective in treating, or at least inhibiting or suppressing, SARS-CoV-2 by inhibiting the interaction of RACK1 with Host Annexin A2 (ANXA2). The present inventors posited a possible mechanism of action, namely inhibiting the interaction between RACK1 and ANXA2, so as to allow the accumulation of (free) ANXA2 (that may subsequently inhibit frameshifting in SARS-CoV-2). As SARS-CoV-2 efficiently uses frameshifting to produce the 1ab polyprotein that gives rise to all of the nsp1-nsp16 proteins, the present inventors posited that the application of the RACK1 inhibitor compounds of the present disclosure will inhibit frameshifting by resulting in the generation of excess free ANXA2, which may inhibit frameshifting by binding to the pseudoknot structure just upstream of the frameshifting site.

Figure 17:
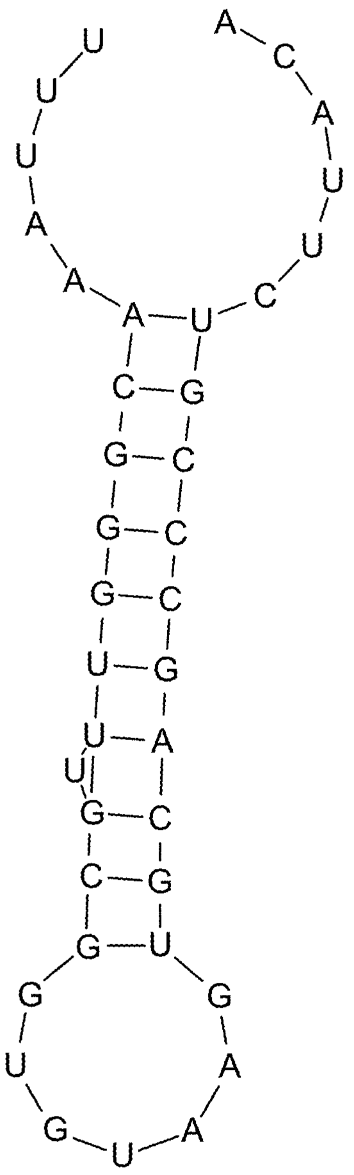
FIG. 17 shows a putative pseudoknot present within the frameshifting site of SARS-CoV-2.

The present inventors identified a putative pseudoknot present within the frameshifting site of SARS-COV-2 (from the SARS-COV-2 Wuhan-Hu-1 isolate deposited under Genbank accession number MN908947), which is depicted in FIG. 17. Note that the slippery site contains the universally conserved slippery site UUUAAAC found in all reported coronaviruses. Huang X, Cheng Q, Du Z ("A genome-wide analysis of RNA pseudoknots that stimulate efficient-1 ribosomal frameshifting or readthrough in animal viruses," *Biomed Res. Int.,* 2013, 2013:984028). The UUUAAACGGGUUUGCGGUGUAAGUGCAGCCCGU-CUUACA (SEQ ID NO: 8) sequence was used to predict the pseudoknot (the slippery site is depicted in bold). The sequence represents 13462 to 13490 bp of SARS-COV-2 of the Wuhan-Hu-1 isolate (Genbank accession number MN908947), the sequence of which can be found at www.ncbi.nlm.nih.gov/nuccore/MN90894 7. To predict the pseudoknot, VSFOLD5 was used (www.rna.it-chiba.ac.jp/~vsfold/vsfold5/). The pseudoknot contains the following structures: Stem 1=7 bp; Stem 2=3 bp; Loop 1=11 bp; Loop 2=1 bp; Loop 3=7 bp. See FIG. 17.

To further confirm this mechanism of action, LC-MS (Liquid Chromatography-Mass Spectrometry) was conducted to determine the effect of RACK1 inhibition on ANXA2 expression. As shown in the following Table 3, SD29-14 treatment resulted in an increased abundance of human ANXA2.

TABLE 3

Statistically significant abundance of Human Annexin A2 protein fragments in response to compound SD29-14. Abundance ratios were calculated by dividing the raw fragment numbers in response to SD29-14 over the DMSO-(no compound) treated samples.

| Annexin A2 Fragment | DMSO abundance | SD29-14 (10 uM) abundance | SD29-14 (100 uM) abundance | Abundance ratio 1 | Abundance ratio 2 | Abundance Ratio Adj. P-Value | Abundance Ratio Adj. P-Value |
|---|---|---|---|---|---|---|---|
| TNQELQEINR (SEQ ID NO: 9) | 43997 | 462054 | 190293 | 10.502 | 4.325 | 0.00060520 | 0.07396129 |
| GVDEVTIVNILTNR (SEQ ID NO: 10) | none | 133381 | 9540 | >100 | >100 | 4.62E−17 | 3.35E−17 |
| DALNIETAIK (SEQ ID NO: 11) | 40916.6 | 317727.9 | 130507.6 | 7.765 | 3.19 | 0.00533 | 0.178878036 |

As Table 3 shows, compound SD29-14 significantly increased the level of (free) human ANXA2, which the inventors considered to be via inhibition of the interaction of ANXA2 protein with RACK1 protein (thereby relieving the sequestering of ANXA2 by RACK1 protein). As described above, the present inventors propose that the increased level of free ANXA2 protein is expected to inhibit the frameshifting efficiency, and thus inhibit SARS-CoV-2 replication.

We claim:

1. A method for inhibiting the replication of a virus that utilizes an internal ribosome entry site in its replication, comprising:

administering a compound, a tautomer, or a pharmaceutically acceptable salt thereof, in an amount effective for inhibiting replication of the virus in cells, and either separately administering another anti-viral drug and/or a pro-drug of the anti-viral drug, or co-administering the anti-viral drug and/or the pro-drug with the compound, its tautomer, or its pharmaceutically acceptable salt, wherein the compound is represented by the formula:

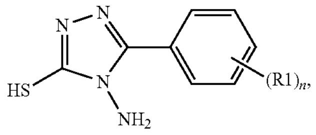

wherein n is 2, R1 represents a halogen atom selected from the group consisting of bromo, chloro, fluoro, and iodo, and R1 is substituted at the 2,4 positions and the 3,5 positions of the phenyl moiety, provided that each R1 can be the same or different; and wherein the anti-viral drug is acyclovir, a pharmaceutically acceptable salt of acyclovir, or a combination thereof, and the pro-drug is valacyclovir, a pharmaceutically acceptable salt of valacyclovir, or a combination thereof.

2. The method according to claim 1, wherein n is 2 and each R1 is the same and represents bromo, chloro or fluoro.

3. The method according to claim 1, wherein the virus is from the family Coronaviridae.

4. The method according to claim 3, wherein the virus is SARS-CoV-2.

5. A method for inhibiting the replication of a virus that utilizes an internal ribosome entry site in its replication, comprising:

administering a compound, a tautomer, or a pharmaceutically acceptable salt thereof, in an amount effective for inhibiting replication of the virus in cells, and either separately administering another anti-viral drug and/or a pro-drug of to the anti-viral drug, or co-administering the anti-viral drug and/or the pro-drug with the compound, its tautomer, or its pharmaceutically acceptable salt wherein the compound is represented by the formula:

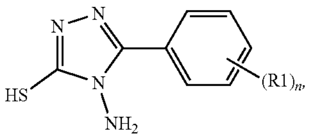

wherein n is 2, and both R1 represent chloro, wherein the anti-viral drug is acyclovir, a pharmaceutically acceptable salt of acyclovir, or a combination thereof, and the pro-drug is valacyclovir, a pharmaceutically acceptable salt of valacyclovir, or a combination thereof.

6. The method according to claim 5, wherein the virus is from the family Coronaviridae.

7. The method according to claim 6, wherein the virus is SARS-COV-2.

8. A method for inhibiting the replication of a virus that utilizes an internal ribosome entry site in its replication, comprising:

administering a compound, a tautomer, or a pharmaceutically acceptable salt thereof, in an amount effective for inhibiting replication of the virus in cells, and either separately administering another anti-viral drug and/or a pro-drug of to the anti-viral drug, or co-administering the anti-viral drug and/or the pro-drug with the compound, its tautomer, or its pharmaceutically acceptable salt, wherein the compound is one or more selected from the group consisting of:

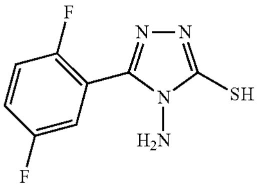

-continued

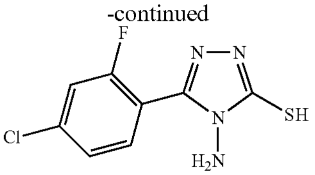

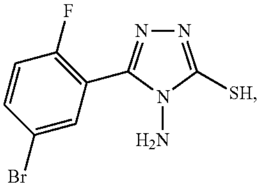

and

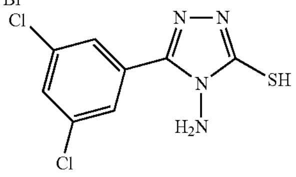

wherein the anti-viral drug is acyclovir, a pharmaceutically acceptable salt of acyclovir, or a combination thereof, and the pro-drug is valacyclovir, a pharmaceutically acceptable salt of valacyclovir, or a combination thereof.

9. The method according to claim 8, wherein the virus is from the family Coronaviridae.

10. The method according to claim 9, wherein the virus is SARS-COV-2.

* * * * *

SEQUENCE LISTING

```
<160> NUMBER OF SEQ ID NOS: 5

<210> SEQ ID NO 1
<211> LENGTH: 17
<212> TYPE: DNA
<213> ORGANISM: Artificial Sequence
<220> FEATURE:
<223> OTHER INFORMATION: primer for HSV-1 ICP0 - forward

<400> SEQUENCE: 1

ctgcgctgcg acacctt                                                17


<210> SEQ ID NO 2
<211> LENGTH: 22
<212> TYPE: DNA
<213> ORGANISM: Artificial Sequence
<220> FEATURE:
<223> OTHER INFORMATION: primer for HSV-1 ICP0 - reverse
```

-continued

<400> SEQUENCE: 2
caattgcatc caggttttca tg 22

<210> SEQ ID NO 3
<211> LENGTH: 21
<212> TYPE: DNA
<213> ORGANISM: Artificial Sequence
<220> FEATURE:
<223> OTHER INFORMATION: primer for beta-actin - forward

<400> SEQUENCE: 3
ggttccgatg ccctgaggct c 21

<210> SEQ ID NO 4
<211> LENGTH: 21
<212> TYPE: DNA
<213> ORGANISM: Artificial Sequence
<220> FEATURE:
<223> OTHER INFORMATION: primer for beta-actin - reverse

<400> SEQUENCE: 4
acttgcggtg cacgatggag g 21

<210> SEQ ID NO 5
<211> LENGTH: 14
<212> TYPE: PRT
<213> ORGANISM: Artificial Sequence
<220> FEATURE:
<223> OTHER INFORMATION: Synthetic peptide sequence

<400> SEQUENCE: 5

Phe Ser Pro Asn Arg Tyr Trp Leu Cys Ala Ala Thr Glu Asn
1 5 10